United States Patent
Gray et al.

(10) Patent No.: US 12,011,174 B2
(45) Date of Patent: Jun. 18, 2024

(54) OCCLUSION SYSTEMS

(71) Applicant: Terumo Corporation, Tokyo (JP)

(72) Inventors: Brian Gray, Tokyo (JP); Anup Dasnurkar, Tokyo (JP); Maricela Walker, Tokyo (JP); Michael Martel, Tokyo (JP); Hiroki Kamiuchi, Tokyo (JP)

(73) Assignee: Terumo Corporation, Tokyo (JP)

( * ) Notice: Subject to any disclaimer, the term of this patent is extended or adjusted under 35 U.S.C. 154(b) by 412 days.

(21) Appl. No.: 17/242,740

(22) Filed: Apr. 28, 2021

(65) Prior Publication Data

US 2021/0330333 A1     Oct. 28, 2021

Related U.S. Application Data

(60) Provisional application No. 63/016,810, filed on Apr. 28, 2020.

(51) Int. Cl.
*A61B 17/12*       (2006.01)
*A61B 17/00*       (2006.01)

(52) U.S. Cl.
CPC .. *A61B 17/12136* (2013.01); *A61B 17/12122* (2013.01); *A61B 2017/00632* (2013.01);
(Continued)

(58) Field of Classification Search
CPC ........ A61B 17/12136; A61B 17/12122; A61B 2017/00632; A61B 2017/00951;
(Continued)

(56) References Cited

U.S. PATENT DOCUMENTS 4,364,392 A * 12/1982 Strother ............. A61B 17/0057
606/195
5,067,489 A    11/1991 Lind
(Continued)

FOREIGN PATENT DOCUMENTS

CN       102438533 A    5/2012
EP       1691879 B1    8/2006
(Continued)

OTHER PUBLICATIONS

WIPO, U.S. International Search Authority, International Search Report and Written Opinion dated Aug. 18, 2021 in International Patent Application No. PCT/US2021/029618, 10 pages.
(Continued)

*Primary Examiner* — Tan-Uyen T Ho
*Assistant Examiner* — David P Stein
(74) *Attorney, Agent, or Firm* — Inskeep IP Group, Inc.

(57) ABSTRACT

An occlusion device with particular utility in occlusion of left atrial appendages is described. The occlusion device utilizes an inflatable balloon comprising a proximal portion to inflate with an inflation fluid delivered by an outer catheter body and conform to a shape of the left atrial appendage and a distal portion to fill with an adhesive delivered by an inner catheter body. The distal portion of the inflatable balloon sticks to the tissue wall of the left atrial appendage. The outer catheter body is configured to position the inner catheter body inside the outer catheter body.

20 Claims, 17 Drawing Sheets

(52) U.S. Cl.
CPC .............. *A61B 2017/00951* (2013.01); *A61B 2017/12095* (2013.01)

(58) Field of Classification Search
CPC ........... A61B 2017/12095; A61B 2017/00893; A61B 17/00491; A61B 2017/1205; A61M 2025/1054
See application file for complete search history.

(56) References Cited

U.S. PATENT DOCUMENTS

| | | | |
|---|---|---|---|
| 5,122,136 A | 6/1992 | Guglielmi et al. |
| 5,330,483 A | 7/1994 | Heaven et al. |
| 5,334,210 A | 8/1994 | Gianturco |
| 5,354,309 A | 10/1994 | Schnepp-Pesch et al. |
| 5,397,331 A | 3/1995 | Himpens et al. |
| 5,466,242 A | 11/1995 | Mori |
| 5,478,331 A | 12/1995 | Heflin et al. |
| 5,496,277 A | 3/1996 | Termin et al. |
| 5,499,995 A | 5/1996 | Teirstein |
| 5,514,093 A | 5/1996 | Ellis et al. |
| 5,632,761 A | 5/1997 | Smith et al. |
| 5,662,711 A | 9/1997 | Douglas |
| 5,713,848 A | 2/1998 | Dubrul |
| 5,718,159 A | 2/1998 | Thompson |
| 5,725,552 A | 3/1998 | Kotula et al. |
| 5,741,333 A | 4/1998 | Frid |
| 5,769,816 A | 6/1998 | Barbut et al. |
| 5,814,062 A | 9/1998 | Sepetka et al. |
| 5,814,064 A | 9/1998 | Daniel et al. |
| 5,846,261 A | 12/1998 | Kotula et al. |
| 5,853,422 A | 12/1998 | Huebsch et al. |
| 5,861,003 A | 1/1999 | Latson et al. |
| 5,868,778 A | 2/1999 | Gershony et al. |
| 5,919,224 A | 7/1999 | Thompson et al. |
| 5,925,060 A | 7/1999 | Forber |
| 5,941,896 A | 8/1999 | Kerr |
| 5,944,738 A | 8/1999 | Amplatz et al. |
| 5,947,997 A | 9/1999 | Pavcnik et al. |
| 5,954,745 A | 9/1999 | Gertler et al. |
| 6,010,498 A | 1/2000 | Guglielmi |
| 6,019,786 A | 2/2000 | Thompson |
| 6,022,336 A | 2/2000 | Zadno-Azizi et al. |
| 6,024,754 A | 2/2000 | Engelson |
| 6,027,520 A | 2/2000 | Tsugita et al. |
| 6,059,814 A | 5/2000 | Ladd |
| 6,066,149 A | 5/2000 | Samson et al. |
| 6,113,641 A | 9/2000 | Leroy et al. |
| 6,142,987 A | 11/2000 | Tsugita |
| 6,152,144 A | 11/2000 | Lesh et al. |
| 6,176,873 B1 | 1/2001 | Ouchi |
| 6,346,117 B1 | 2/2002 | Greenhalgh |
| 6,355,051 B1 | 3/2002 | Sisskind et al. |
| 6,375,668 B1 | 4/2002 | Gifford et al. |
| 6,379,329 B1 * | 4/2002 | Naglreiter ........ A61B 17/12136 604/101.02 |
| 6,428,557 B1 | 8/2002 | Hilaire |
| 6,428,558 B1 | 8/2002 | Jones et al. |
| 6,451,048 B1 | 9/2002 | Berg et al. |
| 6,468,303 B1 | 10/2002 | Amplatz et al. |
| 6,550,177 B1 | 4/2003 | Epple, Jr. |
| 6,585,748 B1 | 7/2003 | Jeffree |
| 6,589,265 B1 | 7/2003 | Palmer et al. |
| 6,652,555 B1 | 11/2003 | VanTassel et al. |
| 6,802,851 B2 | 10/2004 | Jones et al. |
| 6,811,560 B2 | 11/2004 | Jones et al. |
| 6,953,472 B2 | 10/2005 | Palmer et al. |
| 6,994,717 B2 | 2/2006 | Kónya et al. |
| 7,083,632 B2 | 8/2006 | Avellanet et al. |
| 7,122,058 B2 | 10/2006 | Levine et al. |
| 7,195,636 B2 | 3/2007 | Avellanet et al. |
| 7,229,461 B2 | 6/2007 | Chin et al. |
| 7,267,694 B2 | 9/2007 | Levine et al. |
| 7,294,146 B2 | 11/2007 | Chew et al. |
| 7,306,624 B2 | 12/2007 | Yodfat et al. |
| 7,320,065 B2 | 1/2008 | Gosior et al. |
| 7,326,224 B2 | 2/2008 | Houde et al. |
| 7,329,285 B2 | 2/2008 | Levine et al. |
| 7,569,066 B2 | 8/2009 | Gerberding et al. |
| 7,632,291 B2 | 12/2009 | Stephens et al. |
| 7,645,259 B2 | 1/2010 | Goldman |
| 7,665,466 B2 | 2/2010 | Figulla et al. |
| 7,678,129 B1 | 3/2010 | Gesswein et al. |
| 7,691,124 B2 | 4/2010 | Balgobin |
| 7,695,488 B2 | 4/2010 | Berenstein et al. |
| 7,713,282 B2 | 5/2010 | Frazier et al. |
| 7,749,238 B2 | 7/2010 | Corcoran et al. |
| 7,762,943 B2 | 7/2010 | Khairkhahan |
| 7,981,151 B2 | 7/2011 | Rowe |
| 8,034,061 B2 | 10/2011 | Amplatz et al. |
| 8,043,326 B2 | 10/2011 | Hancock et al. |
| 8,060,183 B2 | 11/2011 | Leopold et al. |
| 8,062,251 B2 | 11/2011 | Goldman |
| 8,066,732 B2 | 11/2011 | Paul et al. |
| 8,083,792 B2 | 12/2011 | Boucher et al. |
| 8,142,456 B2 | 3/2012 | Rosqueta et al. |
| 8,152,833 B2 | 4/2012 | Zaver et al. |
| 8,251,948 B2 | 8/2012 | Goldman |
| 8,262,719 B2 | 9/2012 | Erickson et al. |
| 8,280,486 B2 | 10/2012 | Miller et al. |
| 8,308,752 B2 | 11/2012 | Tekulve |
| 8,313,505 B2 | 11/2012 | Amplatz et al. |
| 8,352,014 B2 | 1/2013 | Leipold et al. |
| 8,357,180 B2 | 1/2013 | Feller, III et al. |
| 8,361,111 B2 | 1/2013 | Widomski et al. |
| 8,361,138 B2 | 1/2013 | Adams |
| 8,398,670 B2 | 3/2013 | Amplatz et al. |
| 8,408,212 B2 | 4/2013 | O'Brien et al. |
| 8,425,548 B2 | 4/2013 | Connor |
| 8,433,391 B2 | 4/2013 | Mark |
| 8,442,623 B2 | 5/2013 | Nicoson et al. |
| 8,454,633 B2 | 6/2013 | Amplatz et al. |
| 8,460,366 B2 | 6/2013 | Rowe |
| 8,480,702 B2 | 7/2013 | Kusleika et al. |
| 8,491,612 B2 | 7/2013 | Stopek et al. |
| 8,523,940 B2 | 9/2013 | Richardson et al. |
| 8,636,760 B2 | 1/2014 | Garcia et al. |
| 8,663,301 B2 | 3/2014 | Riina et al. |
| 8,671,815 B2 | 3/2014 | Hancock et al. |
| 8,679,150 B1 | 3/2014 | Janardhan et al. |
| 8,685,055 B2 | 4/2014 | VanTassel et al. |
| 8,690,907 B1 | 4/2014 | Janardhan et al. |
| 8,696,701 B2 | 4/2014 | Becking et al. |
| 8,715,314 B1 | 5/2014 | Janardhan et al. |
| 8,715,315 B1 | 5/2014 | Janardhan et al. |
| 8,715,316 B1 | 5/2014 | Janardhan et al. |
| 8,715,317 B1 | 5/2014 | Janardhan et al. |
| 8,715,338 B2 | 5/2014 | Frid |
| 8,721,676 B1 | 5/2014 | Janardhan et al. |
| 8,721,677 B1 | 5/2014 | Janardhan et al. |
| 8,721,707 B2 | 5/2014 | Boucher et al. |
| 8,728,112 B2 | 5/2014 | Evert et al. |
| 8,728,116 B1 | 5/2014 | Janardhan et al. |
| 8,728,117 B1 | 5/2014 | Janardhan et al. |
| 8,728,141 B2 | 5/2014 | Riina et al. |
| 8,733,618 B1 | 5/2014 | Janardhan et al. |
| 8,734,483 B2 | 5/2014 | Tekulve et al. |
| 8,735,777 B1 | 5/2014 | Janardhan et al. |
| 8,747,432 B1 | 6/2014 | Janardhan et al. |
| 8,747,453 B2 | 6/2014 | Amplatz et al. |
| 8,747,462 B2 | 6/2014 | Hill et al. |
| 8,747,597 B2 | 6/2014 | Rosqueta et al. |
| 8,753,371 B1 | 6/2014 | Janardhan et al. |
| 8,758,426 B2 | 6/2014 | Hood et al. |
| 8,764,772 B2 | 7/2014 | Tekulve |
| 8,764,787 B2 | 7/2014 | Ren |
| 8,777,974 B2 | 7/2014 | Amplatz et al. |
| 8,777,979 B2 | 7/2014 | Shrivastava et al. |
| 8,778,008 B2 | 7/2014 | Amplatz et al. |
| 8,783,151 B1 | 7/2014 | Janardhan et al. |
| 8,784,446 B1 | 7/2014 | Janardhan et al. |
| 8,789,452 B1 | 7/2014 | Janardhan et al. |
| 8,790,365 B1 | 7/2014 | Janardhan et al. |
| 8,795,316 B2 | 8/2014 | Balgobin et al. |

(56) References Cited

U.S. PATENT DOCUMENTS

| | | | |
|---|---|---|---|
| 8,795,319 B2 | 8/2014 | Ryan et al. |
| 8,795,330 B1 | 8/2014 | Janardhan et al. |
| 8,803,030 B1 | 8/2014 | Janardhan et al. |
| 8,813,625 B1 | 8/2014 | Janardhan et al. |
| 8,816,247 B1 | 8/2014 | Janardhan et al. |
| 8,821,529 B2 | 9/2014 | Kariniemi et al. |
| 8,821,849 B2 | 9/2014 | Schwartz |
| 8,828,043 B2 | 9/2014 | Chambers |
| 8,828,045 B1 | 9/2014 | Janardhan et al. |
| 8,828,051 B2 | 9/2014 | Javois et al. |
| 8,845,678 B1 | 9/2014 | Janardhan et al. |
| 8,845,679 B1 | 9/2014 | Janardhan et al. |
| 8,852,227 B1 | 10/2014 | Janardhan et al. |
| 8,859,934 B1 | 10/2014 | Janardhan et al. |
| 8,863,631 B1 | 10/2014 | Janardhan et al. |
| 8,866,049 B1 | 10/2014 | Janardhan et al. |
| 8,869,670 B1 | 10/2014 | Janardhan et al. |
| 8,870,901 B1 | 10/2014 | Janardhan et al. |
| 8,870,910 B1 | 10/2014 | Janardhan et al. |
| 8,872,068 B1 | 10/2014 | Janardhan et al. |
| 8,876,849 B2 | 11/2014 | Kratzberg et al. |
| 8,882,787 B2 | 11/2014 | Brenzel et al. |
| 8,882,797 B2 | 11/2014 | Janardhan et al. |
| 8,895,891 B2 | 11/2014 | Janardhan et al. |
| 8,900,287 B2 | 12/2014 | Amplatz et al. |
| 8,904,914 B2 | 12/2014 | Janardhan et al. |
| 8,905,961 B2 | 12/2014 | Braido et al. |
| 8,906,057 B2 | 12/2014 | Connor et al. |
| 8,910,555 B2 | 12/2014 | Janardhan et al. |
| 8,945,170 B2 | 2/2015 | Paul, Jr. |
| 9,011,476 B2 | 4/2015 | Sideris |
| 9,295,571 B2 | 3/2016 | Newell et al. |
| 9,579,104 B2 | 2/2017 | Beckham et al. |
| 9,770,234 B2 | 9/2017 | Sideris et al. |
| 10,398,441 B2 | 9/2019 | Warner et al. |
| 10,405,866 B2 | 9/2019 | Chakraborty et al. |
| 10,751,182 B2* | 8/2020 | Sutherland ............ A61F 2/2481 |
| 10,952,740 B2 | 3/2021 | Dasnurkar et al. |
| 2001/0000797 A1 | 5/2001 | Mazzochi |
| 2001/0012949 A1 | 8/2001 | Forber |
| 2002/0042628 A1 | 4/2002 | Chin et al. |
| 2002/0082638 A1 | 6/2002 | Porter et al. |
| 2002/0111647 A1 | 8/2002 | Khairkhahan et al. |
| 2002/0123759 A1 | 9/2002 | Amplatz |
| 2002/0143349 A1 | 10/2002 | Gifford, III et al. |
| 2002/0156499 A1 | 10/2002 | Konya et al. |
| 2002/0165572 A1 | 11/2002 | Saadat |
| 2002/0189727 A1 | 12/2002 | Peterson |
| 2003/0023299 A1 | 1/2003 | Amplatz et al. |
| 2003/0199919 A1 | 6/2003 | Palmer et al. |
| 2003/0167068 A1 | 9/2003 | Amplatz |
| 2003/0220666 A1 | 11/2003 | Mirigian et al. |
| 2004/0044361 A1 | 3/2004 | Frazier et al. |
| 2004/0049210 A1 | 3/2004 | VanTassel et al. |
| 2004/0193206 A1 | 9/2004 | Gerberding et al. |
| 2005/0065484 A1 | 3/2005 | Watson, Jr. |
| 2005/0070952 A1 | 3/2005 | Devellian |
| 2005/0228434 A1 | 10/2005 | Amplatz et al. |
| 2005/0234543 A1 | 10/2005 | Glaser et al. |
| 2005/0288706 A1 | 12/2005 | Widomski et al. |
| 2006/0135947 A1 | 6/2006 | Soltesz et al. |
| 2006/0161110 A1 | 7/2006 | Lenker et al. |
| 2006/0206139 A1 | 9/2006 | Tekulve |
| 2006/0241690 A1 | 10/2006 | Amplatz et al. |
| 2006/0247680 A1 | 11/2006 | Amplatz et al. |
| 2007/0055302 A1 | 3/2007 | Henry et al. |
| 2007/0066993 A1 | 3/2007 | Kreidler |
| 2007/0112380 A1 | 5/2007 | Figulla et al. |
| 2007/0135826 A1 | 6/2007 | Zaver et al. |
| 2007/0167980 A1 | 7/2007 | Figulla et al. |
| 2007/0179520 A1 | 8/2007 | West |
| 2007/0233186 A1 | 10/2007 | Meng |
| 2007/0239192 A1 | 10/2007 | Litzenberg et al. |
| 2007/0270891 A1 | 11/2007 | McGuckin |
| 2008/0033480 A1 | 2/2008 | Hardert |
| 2008/0097495 A1 | 4/2008 | Feller, III et al. |
| 2008/0103585 A1 | 5/2008 | Monstadt et al. |
| 2008/0119887 A1 | 5/2008 | Que et al. |
| 2008/0249562 A1 | 10/2008 | Cahill |
| 2008/0262518 A1 | 10/2008 | Freudenthal |
| 2008/0281350 A1 | 11/2008 | Sepetka et al. |
| 2008/0306504 A1 | 12/2008 | Win et al. |
| 2009/0018562 A1 | 1/2009 | Amplatz et al. |
| 2009/0062845 A1 | 3/2009 | Tekulve |
| 2009/0082803 A1 | 3/2009 | Adams et al. |
| 2009/0187214 A1 | 7/2009 | Amplatz et al. |
| 2009/0209855 A1 | 8/2009 | Drilling et al. |
| 2009/0216263 A1 | 8/2009 | Tekulve |
| 2010/0010517 A1 | 1/2010 | Stopek et al. |
| 2010/0030200 A1 | 2/2010 | Strauss et al. |
| 2010/0106235 A1 | 4/2010 | Kariniemi et al. |
| 2010/0160847 A1 | 6/2010 | Braido et al. |
| 2010/0217313 A1* | 8/2010 | Raabe ............ A61B 17/12136 606/213 |
| 2010/0318097 A1 | 12/2010 | Ferrera et al. |
| 2010/0324586 A1 | 12/2010 | Miles et al. |
| 2011/0040324 A1 | 2/2011 | McCarthy et al. |
| 2011/0046719 A1 | 2/2011 | Frid |
| 2011/0082491 A1 | 4/2011 | Sepetka et al. |
| 2011/0118776 A1 | 5/2011 | Chen et al. |
| 2011/0265943 A1 | 11/2011 | Rosqueta et al. |
| 2011/0276080 A1 | 11/2011 | Nigon |
| 2011/0295298 A1 | 12/2011 | Moszner |
| 2011/0301630 A1 | 12/2011 | Hendriksen et al. |
| 2012/0041472 A1 | 2/2012 | Tan et al. |
| 2012/0046683 A1 | 2/2012 | Wilson et al. |
| 2012/0143008 A1 | 6/2012 | Wilkins et al. |
| 2012/0172928 A1 | 7/2012 | Eidenschink et al. |
| 2012/0215152 A1 | 8/2012 | Levine et al. |
| 2012/0239066 A1 | 9/2012 | Levine et al. |
| 2012/0245668 A1 | 9/2012 | Kariniemi et al. |
| 2012/0330341 A1 | 12/2012 | Becking et al. |
| 2012/0330348 A1 | 12/2012 | Strauss et al. |
| 2013/0012979 A1 | 1/2013 | Amplatz et al. |
| 2013/0018413 A1 | 1/2013 | Oral et al. |
| 2013/0085521 A1 | 4/2013 | Lim |
| 2013/0138136 A1 | 5/2013 | Beckham et al. |
| 2013/0190798 A1 | 7/2013 | Kapadia |
| 2013/0211443 A1 | 8/2013 | Cragg et al. |
| 2013/0245667 A1 | 9/2013 | Marchand et al. |
| 2013/0274868 A1 | 10/2013 | Cox et al. |
| 2014/0172001 A1 | 6/2014 | Becking et al. |
| 2014/0172004 A1 | 6/2014 | De Canniere |
| 2014/0222132 A1 | 8/2014 | Boucher et al. |
| 2015/0374483 A1* | 12/2015 | Janardhan .......... B23K 26/1435 606/200 |
| 2016/0192912 A1 | 7/2016 | Kassab et al. |
| 2016/0206419 A1* | 7/2016 | Hebert ............ A61B 17/12177 |
| 2017/0042549 A1 | 2/2017 | Kaplan et al. |
| 2018/0338767 A1 | 11/2018 | Dasnurkar et al. |
| 2019/0328412 A1 | 10/2019 | Mazhar et al. |
| 2020/0015827 A1* | 1/2020 | Anderson ............ A61B 90/39 |
| 2021/0330333 A1 | 10/2021 | Gray et al. |

FOREIGN PATENT DOCUMENTS

| | | |
|---|---|---|
| EP | 1994887 A1 | 11/2008 |
| JP | 2003-529410 A | 10/2003 |
| JP | 2007-519498 A | 7/2007 |
| JP | 2008-536620 A | 9/2008 |
| JP | 2012-523943 A | 10/2012 |
| WO | WO 2000/072909 A1 | 12/2000 |
| WO | WO 2001/030266 A1 | 5/2001 |
| WO | WO 2014/146001 A2 | 9/2004 |
| WO | WO 2005/074814 A2 | 8/2005 |
| WO | WO 2005/074814 A3 | 8/2005 |
| WO | WO 2006/115689 A1 | 11/2006 |
| WO | WO 2010/123821 A1 | 10/2010 |
| WO | WO 2013/005195 A1 | 1/2013 |
| WO | WO 2013/068466 A1 | 5/2013 |
| WO | WO 2014/144980 A1 | 9/2014 |

(56) References Cited

FOREIGN PATENT DOCUMENTS

| | | |
|---|---|---|
| WO | WO 2014/145005 A2 | 9/2014 |
| WO | WO 2020/093012 A1 | 5/2020 |

OTHER PUBLICATIONS

European Patent Office, Extended European Search Report dated Apr. 4, 2024 in European Patent Application No. 21797206.6, 6 pages.

* cited by examiner

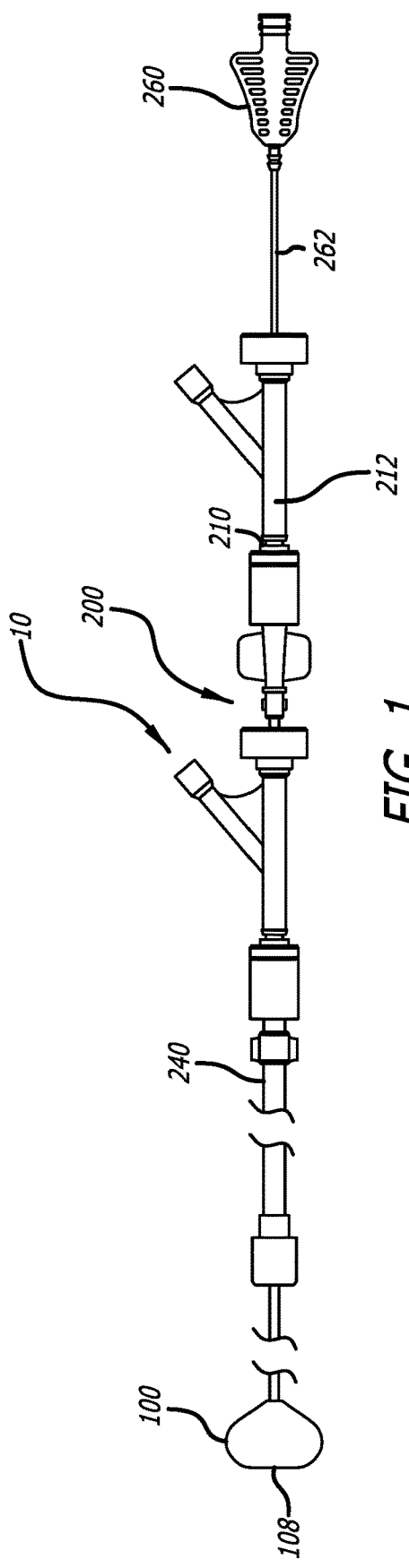
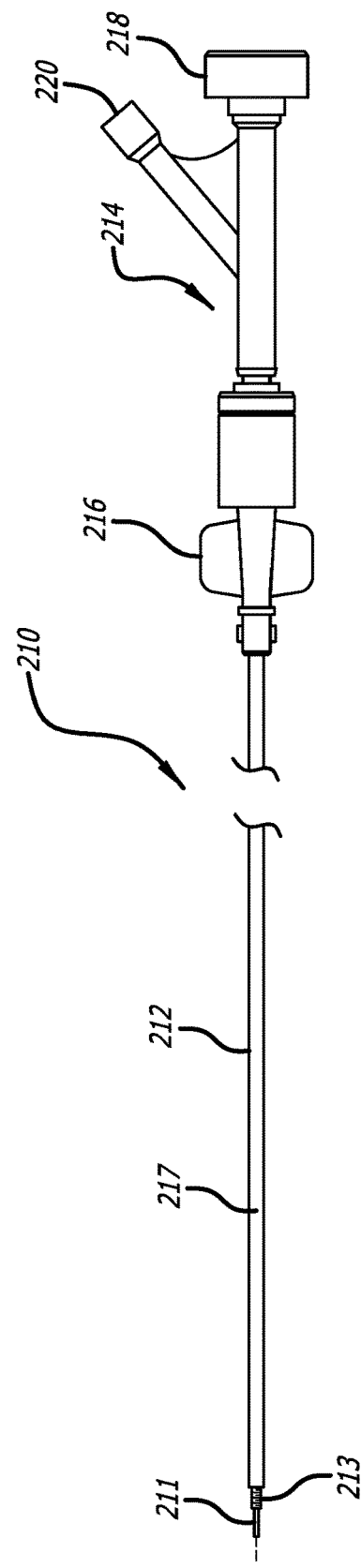

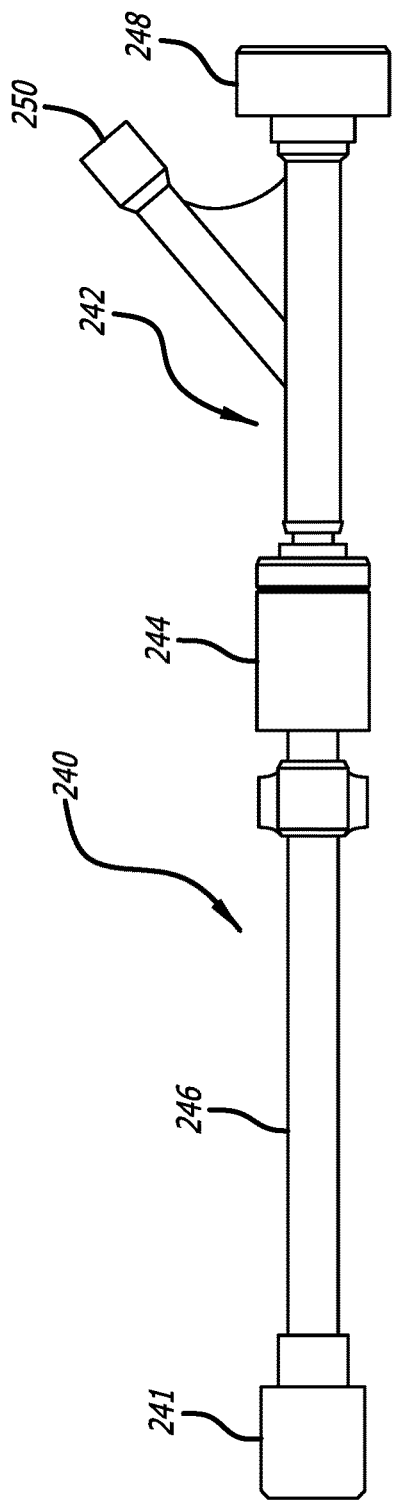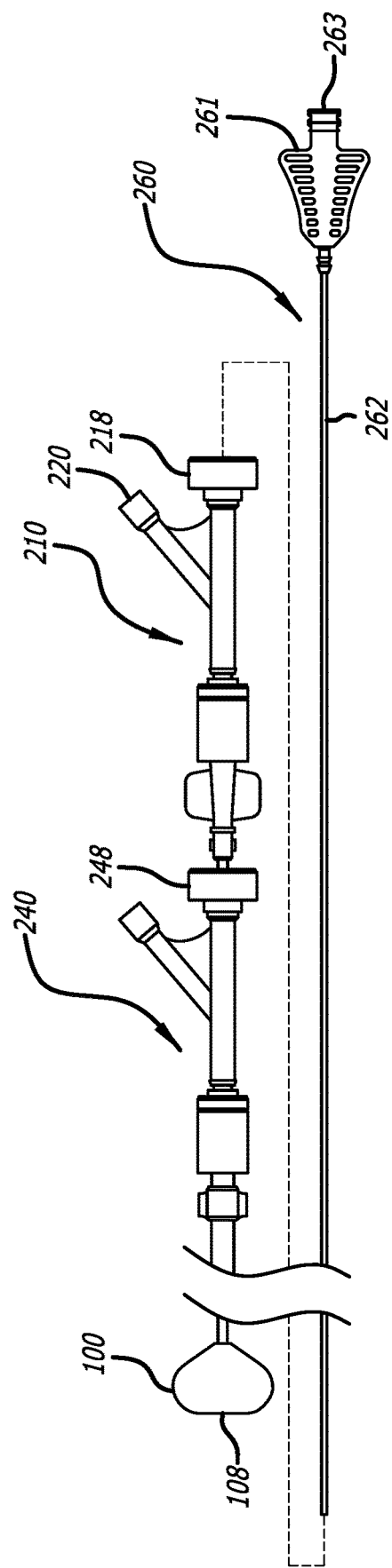
FIG. 3
FIG. 4

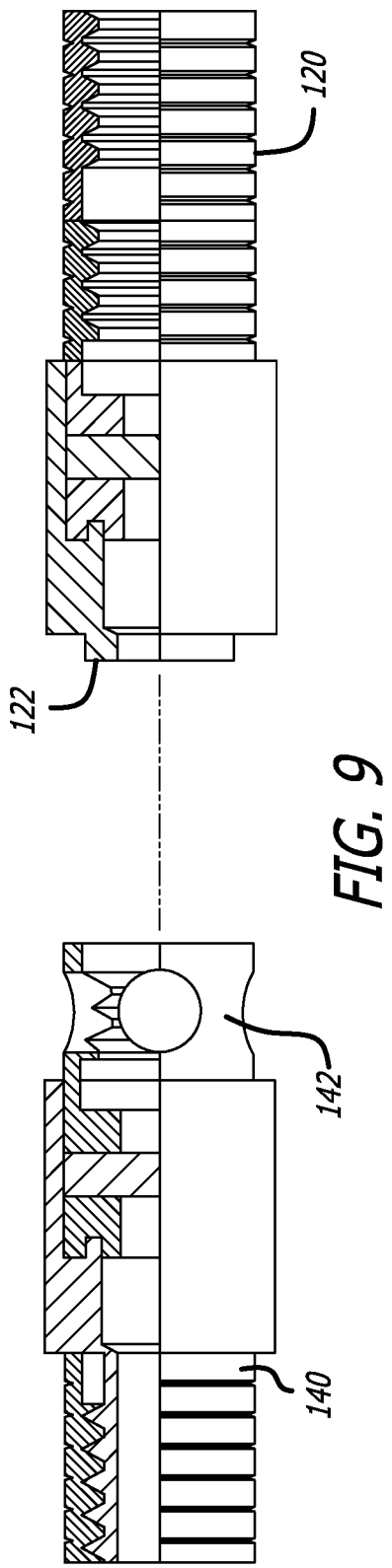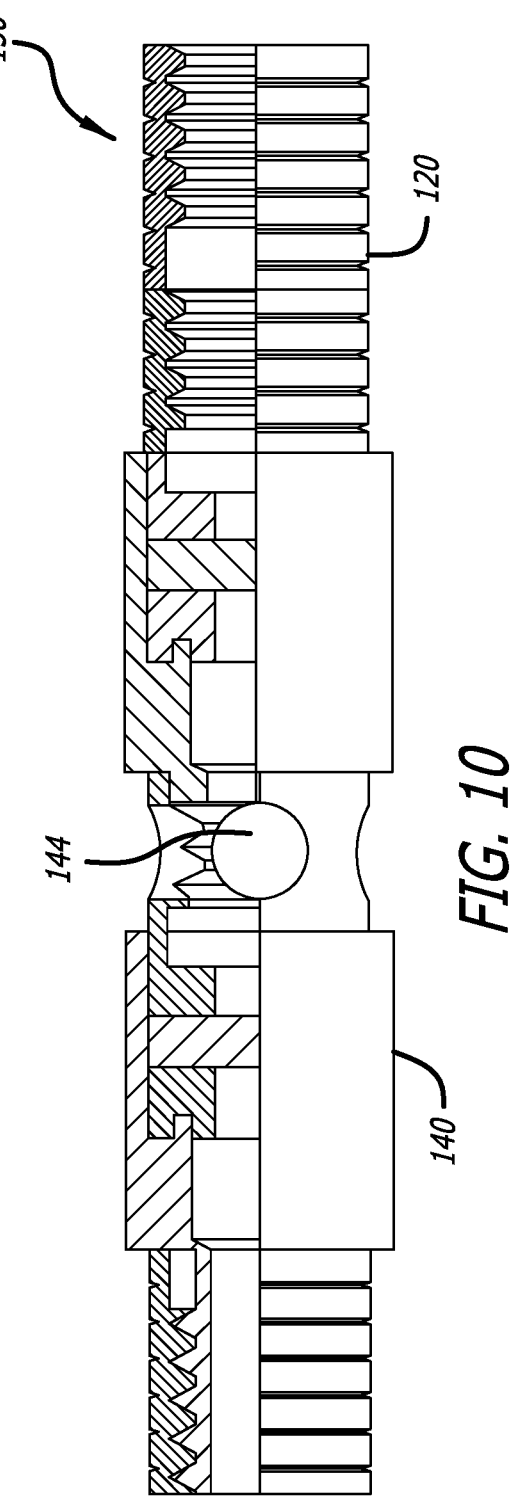

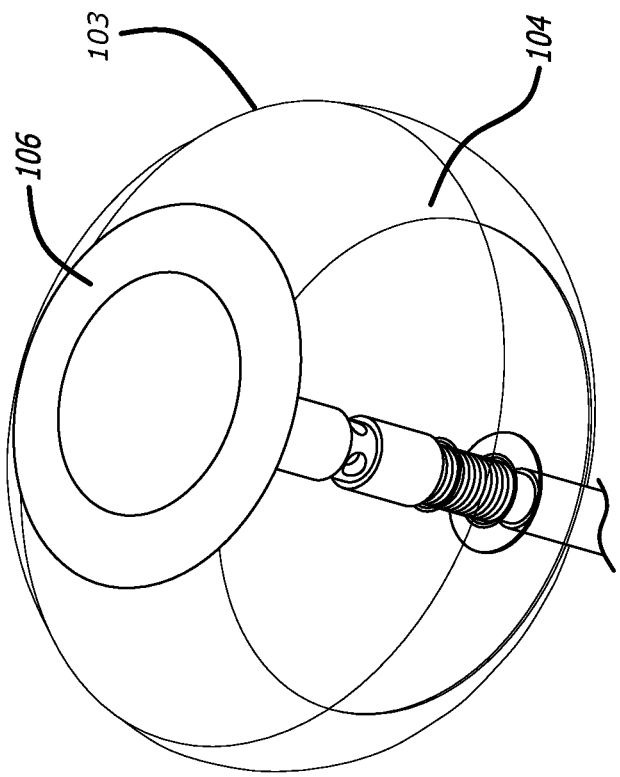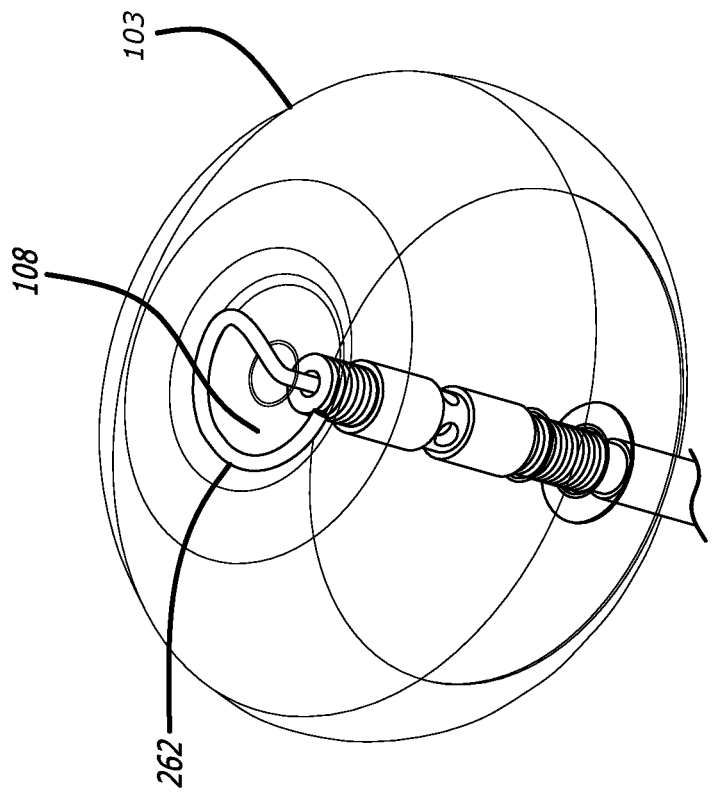
FIG. 19B
FIG. 19A

ODDCLUSION SYSTEMS

RELATED APPLICATIONS

This application is a nonprovisional application of, and claims priority to U.S. Provisional Application Ser. No. 63/016,810 filed Apr. 28, 2020 entitled OCCLUSION SYSTEMS, which is hereby incorporated herein by reference in its entirety.

BACKGROUND OF THE INVENTION

The left atrial appendage (LAA) is a small ear-shaped sac in the muscle wall of the left atrium. For people with atrial fibrillation or an irregular heartbeat, the heart impulse is often irregular which can cause blood to collect in the left atrial appendage and clot over time. These clots can later migrate out of the left atrial appendage, potentially causing a stroke and other complications.

Occlusion is one method of treating a left atrial appendage, where a device or structure is placed within the left atrial appendage to limit blood flow therein. These occlusive structures fill the left atrial appendage space and thereby prevent blood accumulation and clot formation in the area. However, left atrial appendages can be difficult to treat since they typically form complex, irregular shapes thereby making occlusion or filling of the structure difficult. Furthermore, since the left atrial appendage abuts the heart, the region is highly volatile and subject to high pulsation pressure, thereby making it difficult to keep any occlusive device at the target site without migrating. Hence, these factors make it difficult to occlude the left atrial appendage.

Some occlusive devices commonly used for occlusion in other areas of a patient may not be suitable for occlusion of the left atrial appendage. For example, embolic coils are small coils that are frequently used for occlusive purposes in other areas of the vasculature (e.g., neurovascular aneurysms). However, these coils tend to migrate out of the left atrial appendage due to its typically wide ostium or neck region, irregular shape, high pulsatile blood pressure in the region, and its movement with the heart.

To address these factors, some occlusive devices that are specifically designed to treat left atrial appendages utilize barbs to anchor within the left atrial appendage to thereby resist migration. These barbs can puncture the vessel wall and cause tissue damage, which can lead to additional complications. Other devices may forego these anchors, but then suffer from poor apposition relative to the left atrial appendage due to the high pulsatile forces and irregular shape of the region.

The use of a conformable structure, such as an inflatable balloon, may address some of these issues. However, it can be difficult to design a balloon that will be retained in a desired position without deflation or migration. In some instances, the use of adhesive or glue may achieve this.

The use of an inflatable balloon and adhesive can still present several further difficulties. First, both inflation media and an adhesive must be delivered to the balloon with the ability to reliably detach its delivery catheter. Some balloon inflation media can cause the adhesive to prematurely polymerize and therefore may prevent the balloon from detaching from the delivery catheter or may harden prior to reaching the outer surface of the balloon. Further, when the adhesive reaches the outside of the balloon, it can migrate off the balloon, into the blood, and cause unwanted complications in other areas of the patient.

Hence, there is a need for a device which can effectively treat left atrial appendages without the previously described complications while also addressing other deficiencies of the prior art devices not specifically discussed herein.

SUMMARY OF THE INVENTION

An adhesive occlusive system is described herein with particular utility for delivering, inflating, and adhering a balloon within a left atrial appendage. The system may include a catheter assembly configured to delivery inflation fluid and adhesive to a balloon assembly that releasably positioned at a distal end of the catheter assembly.

In one example, the catheter assembly comprises an outer catheter assembly having and an inner catheter assembly that is coaxially and removably positioned inside the outer catheter assembly. The outer catheter assembly is configured to deliver inflation fluid inside a first portion of the balloon assembly (e.g., a proximal portion) to inflate the first portion and the inner catheter assembly is configured to deliver an adhesive to a second portion of the balloon assembly (e.g., a distal portion).

The inner catheter assembly may be removably positioned within an inflation lumen of the outer catheter assembly, and its distal end may extend past a distal end of the outer catheter assembly, allowing it to deliver adhesive to the second or distal portion of the balloon assembly without contacting or mixing with inflation fluid in the first or proximal portion of the balloon assembly.

The second or distal portion of the balloon assembly may comprise a porous distal membrane that may become wet or saturated with adhesive and thereby helps the balloon assembly to adhere to the tissue wall of the left atrial appendage.

A method for occluding blood flow in a left atrial appendage of a patient is also described. This method may comprise providing a catheter assembly and a balloon assembly positioned at a distal end of the catheter assembly, and then advancing the catheter assembly within a patient until the balloon assembly is positioned at least partially or fully within the left atrial appendage.

The balloon assembly is at least partially inflated by delivering an inflation fluid through an inflation lumen of the outer catheter of the catheter assembly so that the balloon assembly expands within and conforms to the left atrial appendage.

Adhesive is delivered to at least a distal end of the balloon assembly through an inner catheter which is removably positioned (e.g., coaxially) inside the outer catheter of the catheter assembly. The inner catheter can be positioned within the inflation lumen of the outer catheter (e.g., coaxially) such that both the inflation fluid and the inner catheter can communicate with the balloon assembly.

The distal portion of the balloon assembly is configured to wet or saturate with adhesive and thereby adhere to an interior of the left atrial appendage. Put another way, the outer surface of the distal portion of the balloon assembly is configured to retain or capture at least some of the adhesive. When the inflation fluid and the adhesive are sufficiently delivered, the inner catheter is removed from the balloon assembly and the outer catheter (e.g., the inflation lumen). Finally, the outer catheter is detached from the balloon assembly (e.g., the outer catheter is unscrewed from the balloon assembly), allowing the outer catheter (and inner catheter if it has not been completely removed from the outer catheter) to be removed from the patient.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which:

FIG. 1 illustrates an occlusive adhesive delivery system comprising a balloon assembly and a catheter assembly, the catheter assembly including a loader assembly, an outer catheter assembly, and an inner catheter assembly.

FIG. 2 illustrates the outer catheter assembly of FIG. 1 comprising a catheter body and a proximal port.

FIG. 3 illustrates the loader assembly of FIG. 1 comprising a distal threaded screw element and a proximal port.

FIG. 4 illustrates the attachments among the balloon assembly, loader assembly, outer catheter assembly and inner catheter assembly of FIG. 1.

FIG. 9 illustrates side views of the proximal valve and distal valve illustrated in FIGS. 7A and 8A.

FIG. 10 illustrates side view of the valve assembly of FIG. 6.

FIG. 19A illustrates a top view of a distal depression or indentation of the balloon assembly of FIG. 5 when a distal membrane of the distal portion is absent.

FIG. 19B illustrates a top view of the distal membrane of the distal portion attached to the proximal portion of the balloon assembly of FIG. 5 around the perimeter of the distal membrane.

DESCRIPTION OF EMBODIMENTS

Figure 5:
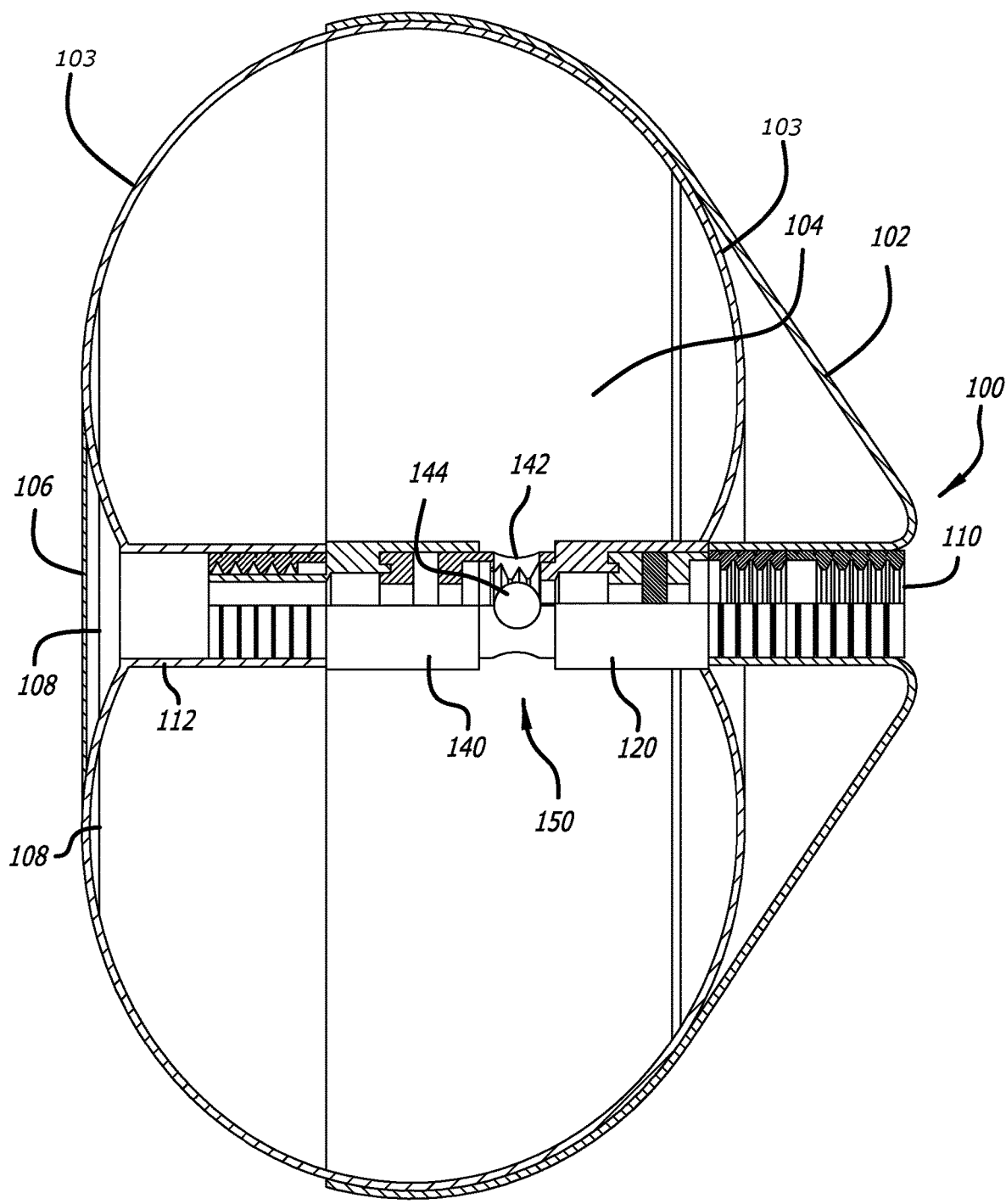
FIG. 5 illustrates the balloon assembly of FIG. 1 with the balloon having a proximal portion and a distal portion in an inflated configuration.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Left atrial appendages are typically difficult to treat since they are located in or near the heart and therefore are exposed to high pulsatile blood pressure, making it difficult to position and maintain an occlusive device in the target area without it migrating. Furthermore, the left atrial appendage often has an irregular shape making it difficult to size and occlude the area.

Inflatable objects such as balloons can provide certain advantages in terms of their conformability to the treatment site and their generally non-traumatic nature. However, this conformable nature can lead to additional challenges as the lack of rigidity from such a structure can make it difficult to maintain a balloon at the exact treatment location without migration. Hence, proper seating of the occlusive balloon is important to create a sufficient barrier to blood entry.

Additionally, such an occlusive balloon typically must include a mechanism to retain its position within the left atrial appendage, once properly seated. Mechanical anchoring features, such as barbs or pins, can be difficult to incorporate on inflatable balloons and can result in undesirable inflammation of the surrounding tissue. In some circumstances, adhesives can provide a more compatible anchoring mechanism for an occlusion balloon since it can immediately adhere to the tissue wall of the left atrial appendage. However, adhesive can migrate within the patient's blood to other locations in the vascular system, depending on the amount of adhesive and how it is released, which can result in undesirable complications, such as stroke.

Described herein is an apparatus and method for treatment of a left atrial appendage. In one example, an inflatable balloon is expanded within the left atrial appendage and adhered to an internal wall, such as the muscle wall of the left atrium occluding the ostium, to thereby block blood flow therein. The balloon and a catheter system can be configured to supply adhesive to an exterior surface of the balloon sufficient to adhere the balloon within the left atrial appendage but while also substantially retaining the adhesive between only the surface of the balloon and the membrane attached to the balloon. The membrane acts as a conduit between the balloon and adhesive, facilitating contact of the implant to the left atrial appendage tissue. For example, the distal innermost facing balloon surface can be configured such that the fabric covering becomes "wetted" or saturated with adhesive without excess adhesive escaping into the patient's blood. The fabric membrane is preferably configured to absorb a specific volume of adhesive. By injecting less than that that threshold volume, excess adhesive escaping from the membrane is prevented or minimized. The adhesive remains held in the membrane's matrix where it then begins to polymerize on contact with the blood. Any portion of the membrane that contacts the appendage wall then becomes attached. Such a configuration may help prevent migration of the adhesive out of the left atrial appendage to other areas of the patient's vascular system, which may result in complications, such as stroke.

In one example shown in FIG. 1, an occlusive adhesive delivery system 10 comprises a balloon assembly 100 positioned at or removably connected to a delivery catheter assembly 200. The delivery catheter assembly 200 is generally configured to position the balloon assembly 100 within a left atrial appendage, inflate the balloon assembly 100, deliver adhesive to an exterior of the balloon assembly 100, and detach the balloon assembly 100 (though, not necessarily in that order as discussed further below).

In one example, the delivery catheter assembly 200 includes an outer catheter assembly 210, an inner catheter assembly 260, and a loader assembly 240. The outer catheter assembly 210 may be configured to act as a conduit for both the inflation fluid of the balloon assembly 100 and for passage of the inner catheter assembly 260 which extends into the balloon assembly 100. The inner catheter assembly 260 provides a lumen into a distal end of the balloon assembly 100 for delivering adhesive and can be removed during the procedure as discussed later in this specification. The loader assembly 250 is an optional component that can assist in loading the outer catheter assembly 210 into an introducer sheath that has been placed into the patient. All of these components are discussed in more detail below.

Figure 21:
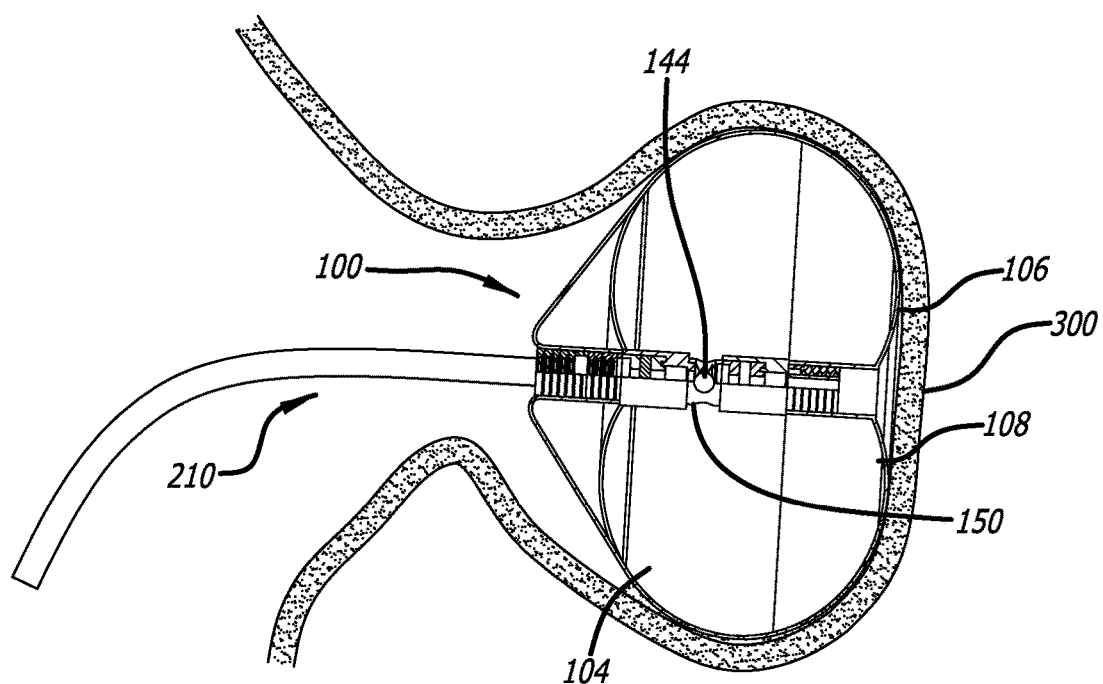
FIG. 21 illustrates the occlusive adhesive delivery system of FIG. 1 used in a treatment region when the balloon assembly is in an inflated state.
Figure 22:
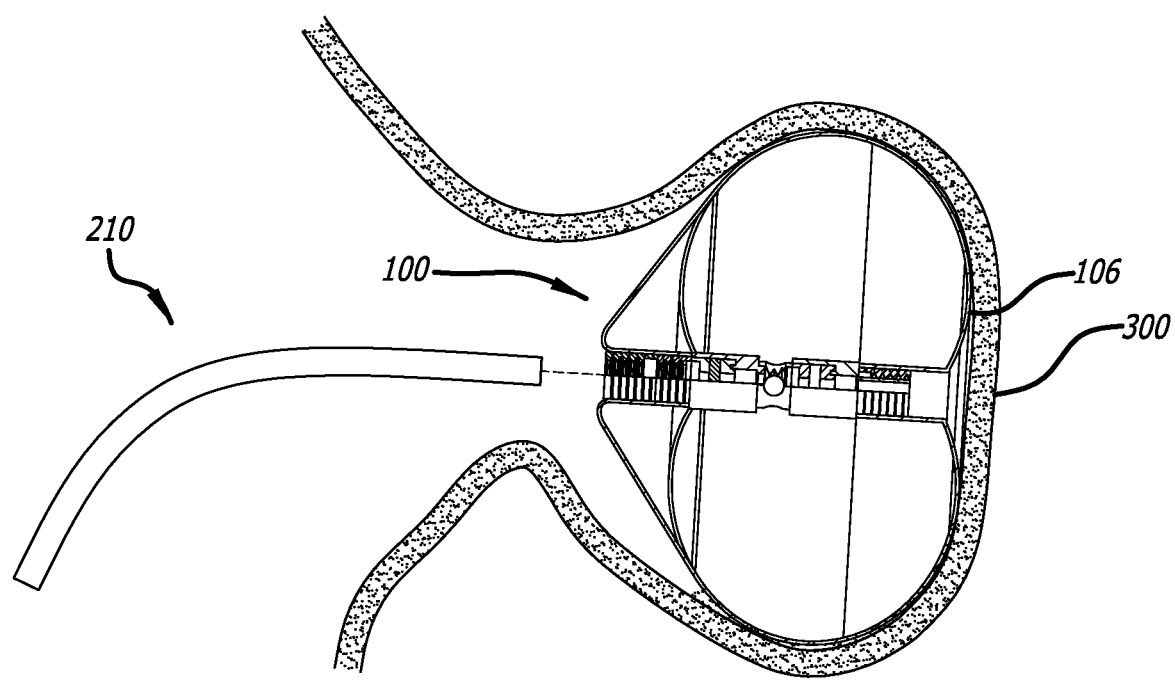
FIG. 22 illustrates the balloon assembly of the occlusive adhesive delivery system of FIG. 1 is left inside the left atrial appendage and the outer catheter assembly of FIG. 1 is removed at the end of the procedure.

The balloon assembly 100 of the occlusion system 10 comprises an inflatable balloon having an inflatable proximal portion 104 and a distal 108 portion, as shown in FIGS. 5 and 15-18. The proximal portion 104 of the balloon assembly 100 is configured to be expanded with an inflation fluid, for example saline and/or contrast agent, while the distal portion 108 of the balloon is configured to receive an adhesive, such as a tissue adhesive. Inside the left atrial appendage 300, as shown in FIGS. 21 and 22, at least an exterior surface of the distal membrane 106 of the distal portion 108 of the balloon assembly 100 is adhered to an internal wall, such as the muscle wall, of the left atrial appendage and the proximal portion 104 of the balloon assembly 100 fills in the cavity of the appendage, preferably extending to the neck or ostium so that blood flow is blocked from entering. Over time, endothelial or tissue growth on the proximal portion 104 of the balloon assembly 100 will eventually seal off the left atrial appendage.

In one example, the proximal inflatable portion 104 of the balloon assembly 100 is formed from an enclosed balloon material 103 that is configured to contain or be substantially impenetrable to fluid, such that the inflation fluid injected into the proximal inflatable portion 104 can be retained. In this way, the material 103 can be thought of as a non-permeable or substantially non-permeable membrane configured to keep the inflation fluid within the balloon, or a barrier element. The balloon membrane 103 can be composed of an elastic and soft material such as polyurethane that resists degradation upon exposure to blood. In one example, the proximal inflatable portion 104 forms a distally-facing depression or circular/conical indentation when inflated, which creates a space or pocket for the distal portion 108. The distal depression or circular indentation is best shown in FIG. 19A in which the top portion of this distal indentation is shown in an uncovered state (i.e., without other components of the distal portion 108). An adhesive-absorbing membrane 106 can be fixed over the depression to create the pocket or enclosed cavity of the distal portion 108, as shown best in FIGS. 5 and 19B. The attachment between the membrane 106 and the proximal inflatable portion 104 can be formed around the perimeter of the distal membrane 106 and the perimeter of the distal depression of the inflatable proximal portion 104. The membrane 106 can be configured such that it is somewhat tight across so that the middle, unattached portion of the distal membrane 106 moves away from the proximal portion 104 as the proximal portion 104 is inflated, as can be seen in FIGS. 5 and 19B. Alternately, the membrane 106 may initially have some slack when the proximal portion 104 is inflated, allowing the addition of adhesive into the distal portion 108 to inflate the cavity and become tight.

In another example, the balloon assembly 100 may include a partition separating the distal portion 108 of the balloon which is filled with adhesive from the more proximal portion 104 of the balloon assembly 100 which is filled with inflation fluid. In other words, the balloon assembly 100 itself is formed of a contiguous balloon element which has a partition added to it to separate it into an inflation fluid receiving proximal portion 104, and an adhesive receiving distal portion 108. In such an example, the balloon material at the distal end of the balloon assembly 100 include a plurality of pores covered by the adhesive-retaining membrane 106, which helps create a saturated or "wet" surface of the balloon assembly 100.

As previously discussed, it can be undesirable for adhesive to be released from the balloon assembly 100 into the patient's blood, since the adhesive can travel to other locations in the vascular system and cause complications, such as stroke. The balloon assembly 100 can help minimize or even eliminate the release of excess adhesive by allowing the adhesive to seep or saturate into the material of the membrane 106 and "wet" the exterior surface of the membrane 106 without releasing excess amounts of the adhesive into surrounding blood. For example, the membrane 106 may be composed of a knitted or mesh material configured to absorb adhesive, as shown in FIG. 5, comprising relatively small pores. The membrane 106 becomes sticky when the distal portion 108 (e.g., a distal compartment) is filled with adhesive and the adhesive seeps from inside of the distal portion 108 to the outside through the smaller pores of the membrane 106. Through this process, the outside surface of the membrane 106 becomes wet and sticky, which allows it to stick to the walls of the left atrial appendix. Additionally, only a relatively small portion of the distal end of the balloon assembly 100 becomes saturated, damp, and/or sticky with adhesive. Therefore, by limiting external exposure of the adhesive to only the distal end, it may be even further prevented from passing into the patient's blood stream to cause complications.

One example of the adhesive absorbing membrane 106 comprises relatively small pores and allows only a small amount of adhesive to diffuse through these pores from inside of the distal portion 108 of the balloon assembly 100 to the outer surface of the membrane 106 to lightly saturate the outer surface of the membrane 106 with the adhesive and to help stick the outer surface of the membrane 106 to the muscle walls of the treatment site, as seen in FIG. 21. The adhesive absorbing membrane 106 is preferably configured to absorb a specific and predetermined volume of adhesive. By injecting less than that that threshold volume, excess adhesive escaping from the membrane is minimized. The adhesive remains held in the membrane's matrix where it then begins to polymerize on contact with the blood. Any portion of the membrane that contacts the appendage wall then becomes attached.

The inner surface of the membrane 106 (i.e., the area contained within distal portion 108 of the balloon assembly 100) is directly exposed to the adhesive since the adhesive fills the distal portion 108 of the balloon assembly 100. However, the outside (or opposite) surface of the membrane 106 also becomes wetted or saturated upon exposure. The membrane pores of the membrane 106 are configured to generally prevent drops or droplets of adhesive from forming on the outer surface of the membrane 106 and being released into the blood, while still allowing the adhesive to be exposed or saturated so as to stick to tissue of the walls of left atrium appendage when in contact.

In one example, the adhesive absorbing membrane 106 is composed of a woven or knit fabric material that can include a plurality of fibers forming a series of interlocking loops as part of its fabric weaving pattern. A knit material may allow for uniform expansion in all directions, which can be helpful to help accommodate the compression and expansion of the balloon assembly 100. Knit material also tends to be thinner and more elastic in this regard. In another example, non-knit materials can be used if it can saturate or retain a quantity of adhesive within its layer or layers. For example, a membrane 106 may be formed from a plurality of polymer sheets that each of a plurality of pores created through them. Unlike a single sheet with pores in which an adhesive may immediately pass completely through, the multiple porous sheets may allow the adhesive to be retained between sheets while also having a path to pass through all layers. In another example, the membrane 106 may comprise a polymer sheet with a plurality of pores and a plurality of very small finger-like elements or fibers extending outward on the outer surface to retain the adhesive.

In one example, the adhesive absorbing membrane 106 is composed of a single layer and in another example the adhesive absorbing membrane 106 is composed of two or more layers, which may help retain more adhesive without substantially releasing the adhesive into the blood.

In one example, the membrane 106 of the balloon assembly 100 comprises pores having pore sizes within an inclusive range of 3 microns-10 microns. Note, these pores may not be round due to the knitting or weaving pattern used and therefore may have an elongated shape with different lengths and widths, both of which may be captured in the example pore size range. A 13 denier high shrink PET fiber can be used woven or knitted together to achieve a target course count of about 120 courses per inch. In one example, the membrane 106 has a thickness within an inclusive range of about 0.001 inch to about 0.003 inch, and more specifically can be about 0.0025 inch in thickness. The fabric of the membrane 106 is preferably configured to retain strength, especially after saturation with adhesive, to prevent the fabric from tearing under repeated loadings (e.g., heart beats).

In some examples, 0.5 ml adhesive is sufficient to stick the outer surface of the knit membrane 106 of the balloon assembly 100 to the tissue wall of the left atrium appendage 300. Hence, the membrane 106 is configured to absorb, saturate, and contain about 0.5 ml or more of adhesive without releasing it into the surrounding blood of the patient. However, different amounts of adhesive can be configured to be absorbed by the membrane 106 such as a range inclusive of 0.1 to 1 ml (e.g., about 0.1, 0.2, 0.3, 0.4, 0.5, 0.6, 0.7, 0.8. 0.9, or 1 ml).

In one example, the membrane 106 comprises a woven PET (polyethylene terephthalate, also known as Dacron), whereby relatively long strands of PET are woven together to form a fabric-like material configured to saturate and contain a predetermined amount of adhesive (e.g., about 0.5 ml).

In some examples, the membrane 106 of the distal portion 108 is attached to the polyurethane surface of the proximal portion 104 of the balloon assembly 100 around the perimeter of the membrane 106 with UV cured glue, as best seen in FIG. 19B. This helps the adhesive maintain a function of saturating only the membrane 106, at least immediately. Once saturated, some adhesive in the membrane 106 may migrate a short distance into the surface of the proximal portion 104 and into its outer endothelial growth material or fabric layer 102.

As previously discussed, the proximal portion 104 is inflated with saline or contrast agent to increase the size of the balloon assembly 100 once positioned within the left atrial appendage. In an inflated state, the surface of the proximal portion 104 can be located immediately adjacent to the neck of the ostium, as best seen in FIG. 21. The proximal portion 104 of the balloon assembly 100 seats next to the neck of the ostium and thereby blocks the blood flow inside the left atrium appendage. The ostium of the left atrial appendage will eventually seal off once the endothelial or tissue will grow on the proximal portion 104 of the balloon assembly 100.

Figure 14:
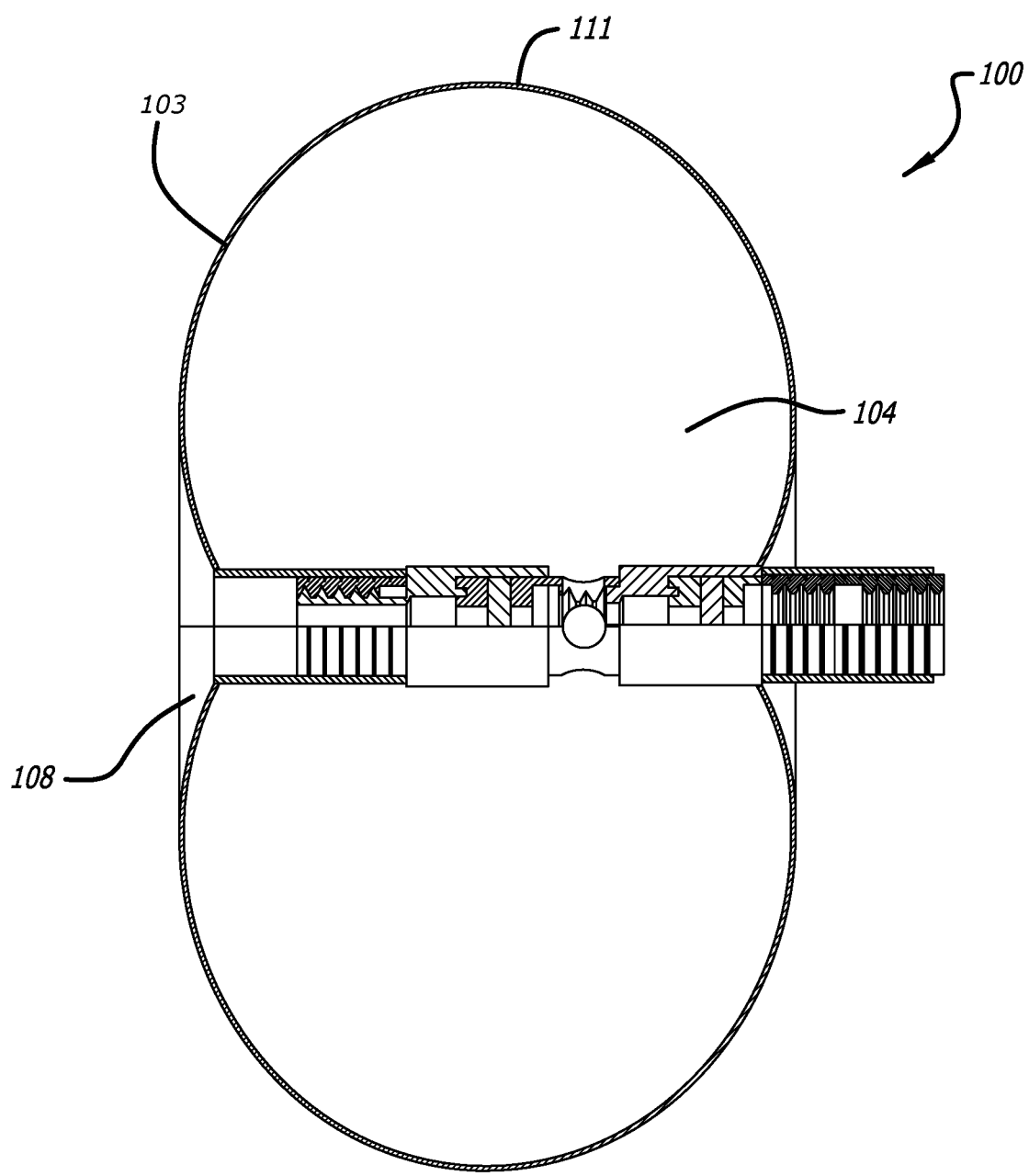
FIG. 14 illustrates the most radially expanded configuration of the balloon assembly of FIG. 5.
Figure 15:
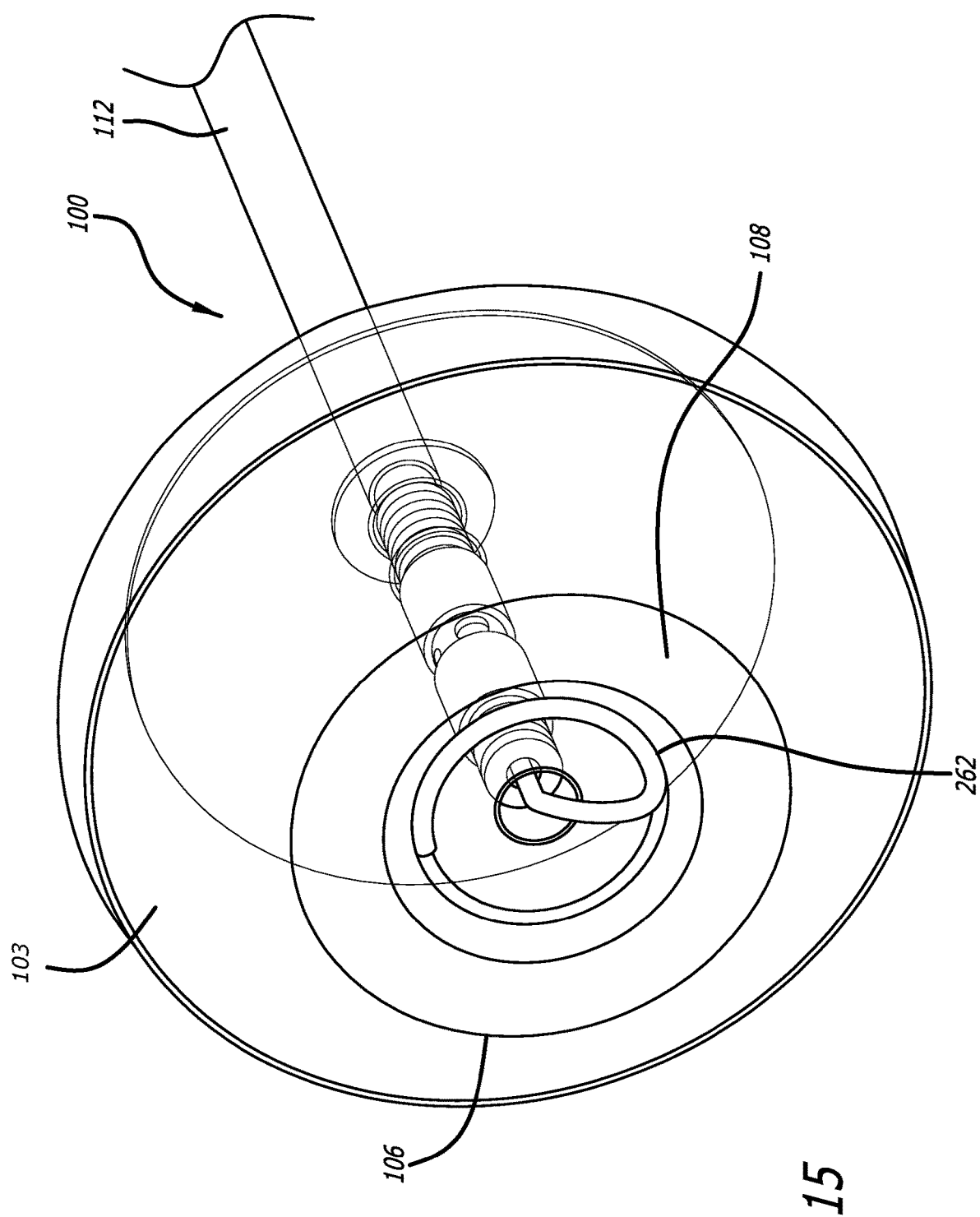
FIG. 15 illustrates a perspective view of the distal portion of the balloon assembly with a distal porous membrane and the catheter body of the inner catheter assembly inside the distal portion of the balloon assembly.
Figure 16:
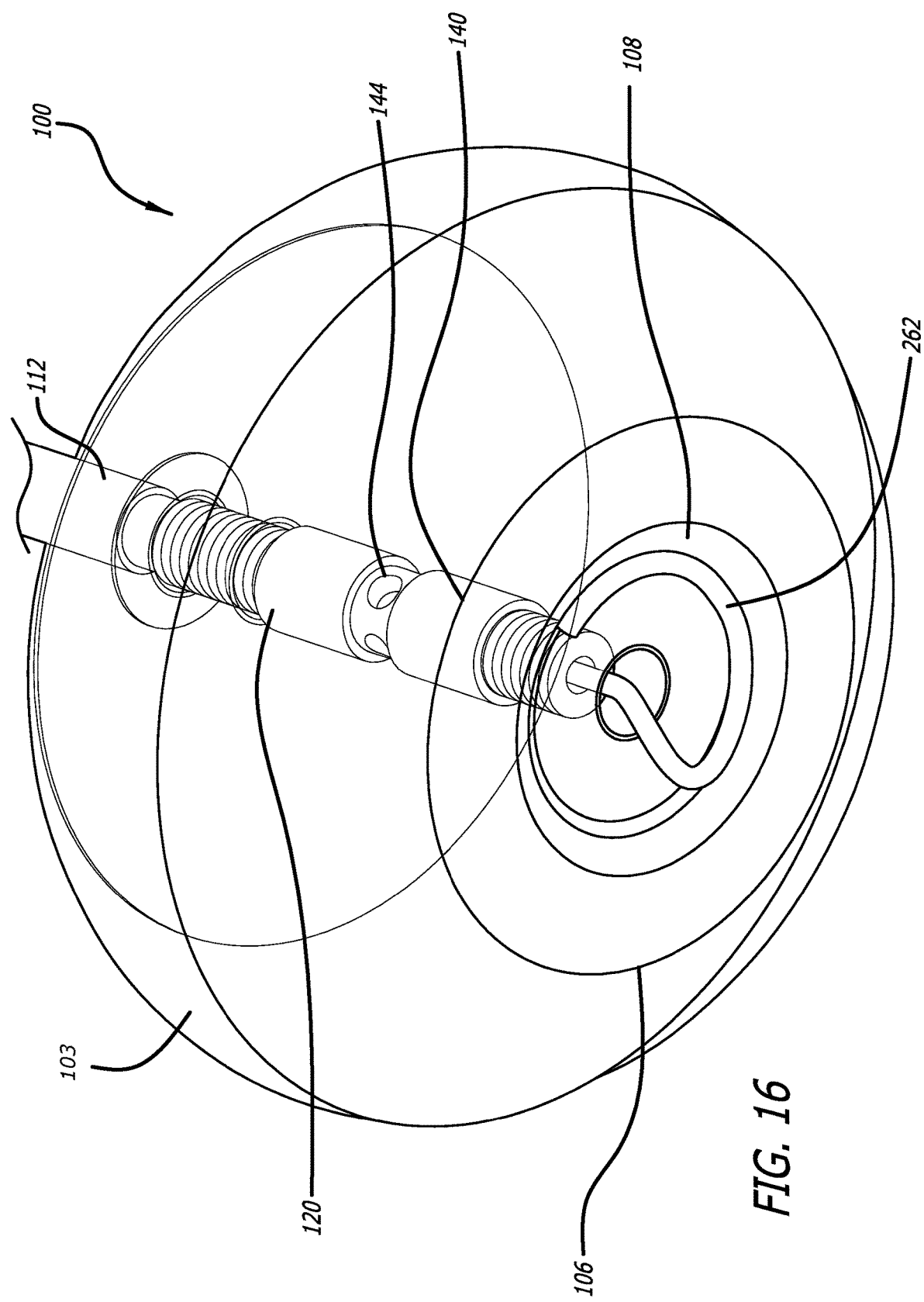
FIG. 16 illustrates a perspective view of the distal portion of the balloon assembly with a distal porous membrane and the catheter body of the inner catheter assembly inside the distal portion of the balloon assembly.
Figure 17:
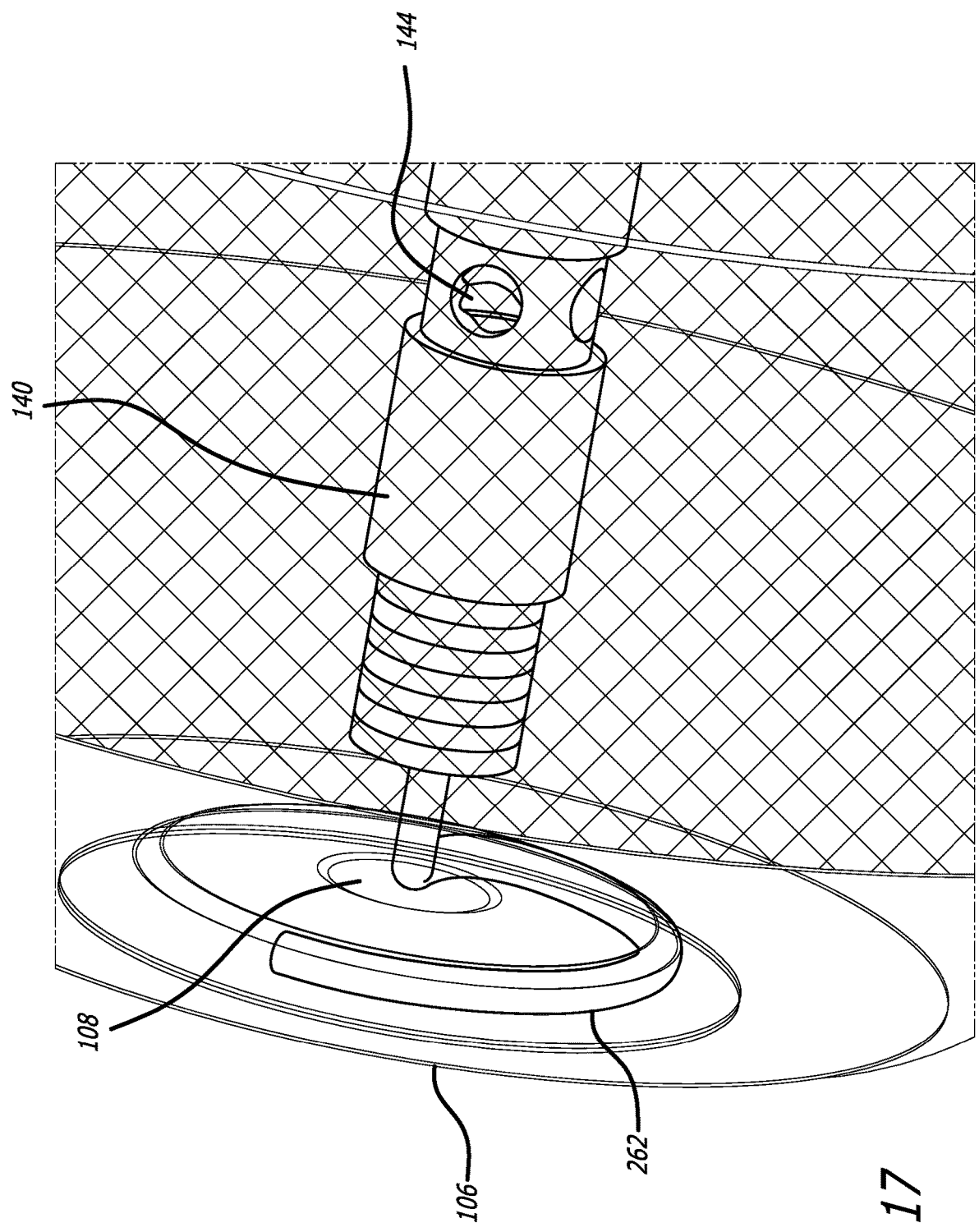
FIG. 17 illustrates a perspective view of the distal portion of the balloon assembly with a distal porous membrane and the catheter body of the inner catheter assembly inside the distal portion of the balloon assembly.
Figure 18:
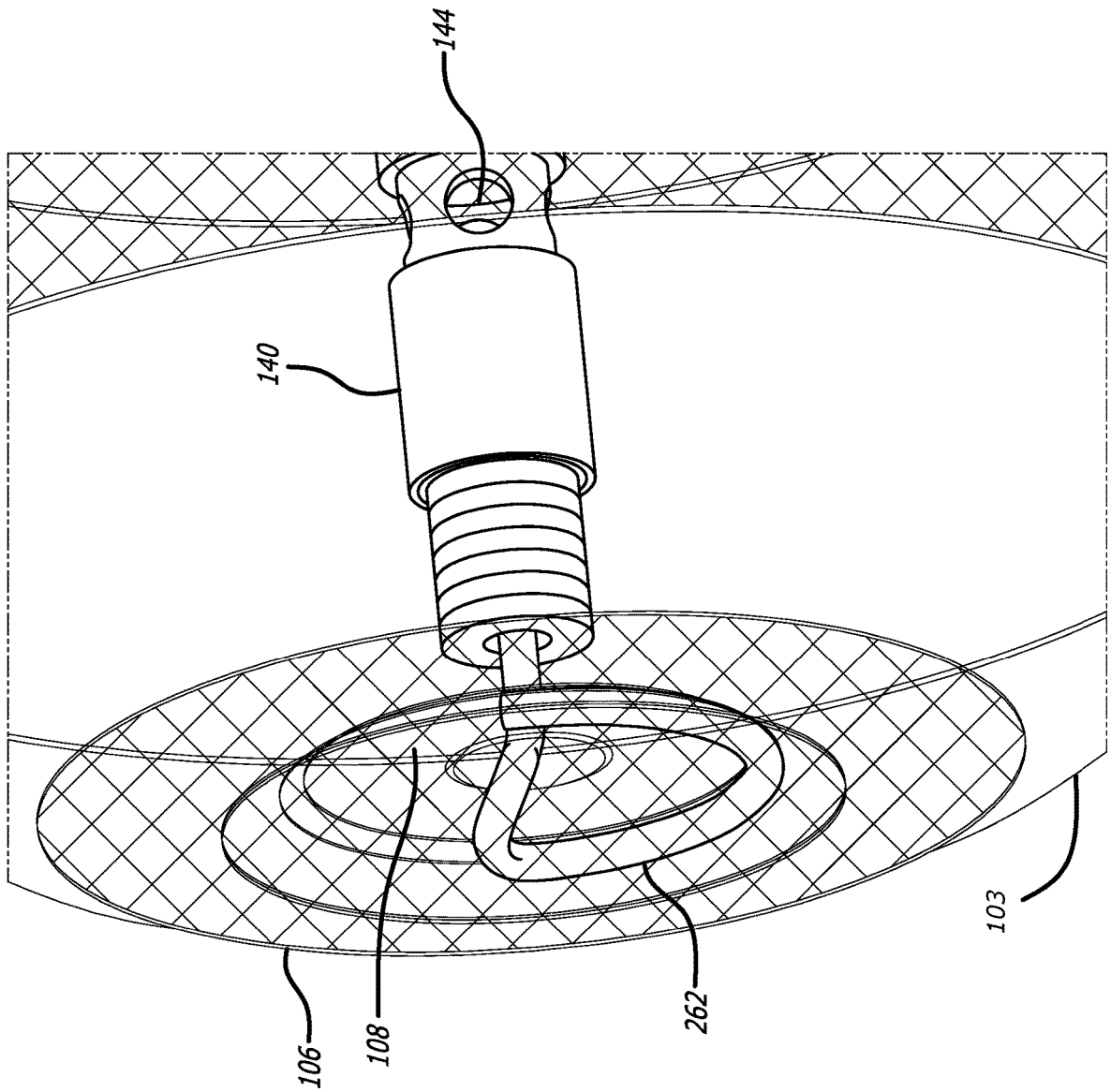
FIG. 18 illustrate a perspective view of the distal portion of the balloon assembly with a distal porous membrane and the catheter body of the inner catheter assembly inside the distal portion of the balloon assembly.

In one example, the proximal portion 104 of the balloon assembly 100, which inflates with inflation fluid, can include an outer endothelial growth material or fabric layer 102 along all or one or more selective portions to encourage the growth of endothelium or tissue to seal off the treatment site (e.g., left atrial appendage) over time. In one example, the medial portion 111 of the balloon assembly 100 (the most radially expansile section which radially "juts out" the most) may utilize this conformable material or fabric 102, as shown in FIG. 14. In another example, the proximal portion 104 may utilize this conformable endothelial growth material or fabric 102 to encourage tissue growth right along the neck of the treatment site (e.g., left atrial appendage) 300 (FIG. 21). In another example, the entire outer portion of the proximal portion 104, aside from the membrane 106, can be covered with the endothelial growth material or fabric 102. While the membrane 106 is configured to retain or saturate with adhesive, the fabric is configured to encourage tissue ingrowth. Hence, pore size may not be critical for such ingrowth and relatively large pore sizes may provide somewhat better ingrowth performance. Preferably the thickness of the endothelial growth material or fabric 102 is relatively thin, so as to maintain a smaller profile of the balloon assembly 100 when deflated.

The fabric surface 102, in one example, is composed of a soft material to encourage tissue growth, such as spun PET (polyethylene terephthalate). Small PET fibers are spun with an adhesive together and pressed into a thin sheet. These small fibers create a soft surface to encourage tissue growth, while the adhesive binds the fibers together and allows them to be pressed into a thin sheet to be added to the balloon. Instead of spinning fibers with adhesive, other techniques are possible for combining the fibers with adhesive, such as weaving, staple nonwoven techniques, melt-blown techniques, spunlaid nonwoven techniques, flashspun techniques, or bonding techniques. In one specific example, individual fibers are about 0.2" long with a fiber diameter gf 6 micrometer and the areal weight was 8 g/m^2. It is desirable to create this layer to be as thin as possible, such as within an inclusive range of 0.002 inch to 0.003 inch. In some examples, it may take 6-9 months to full tissue growth and the balloon assembly 100 and the balloon assembly 100 is configured to remain full/inflated long enough until tissue ingrowth is complete.

Figure 6:
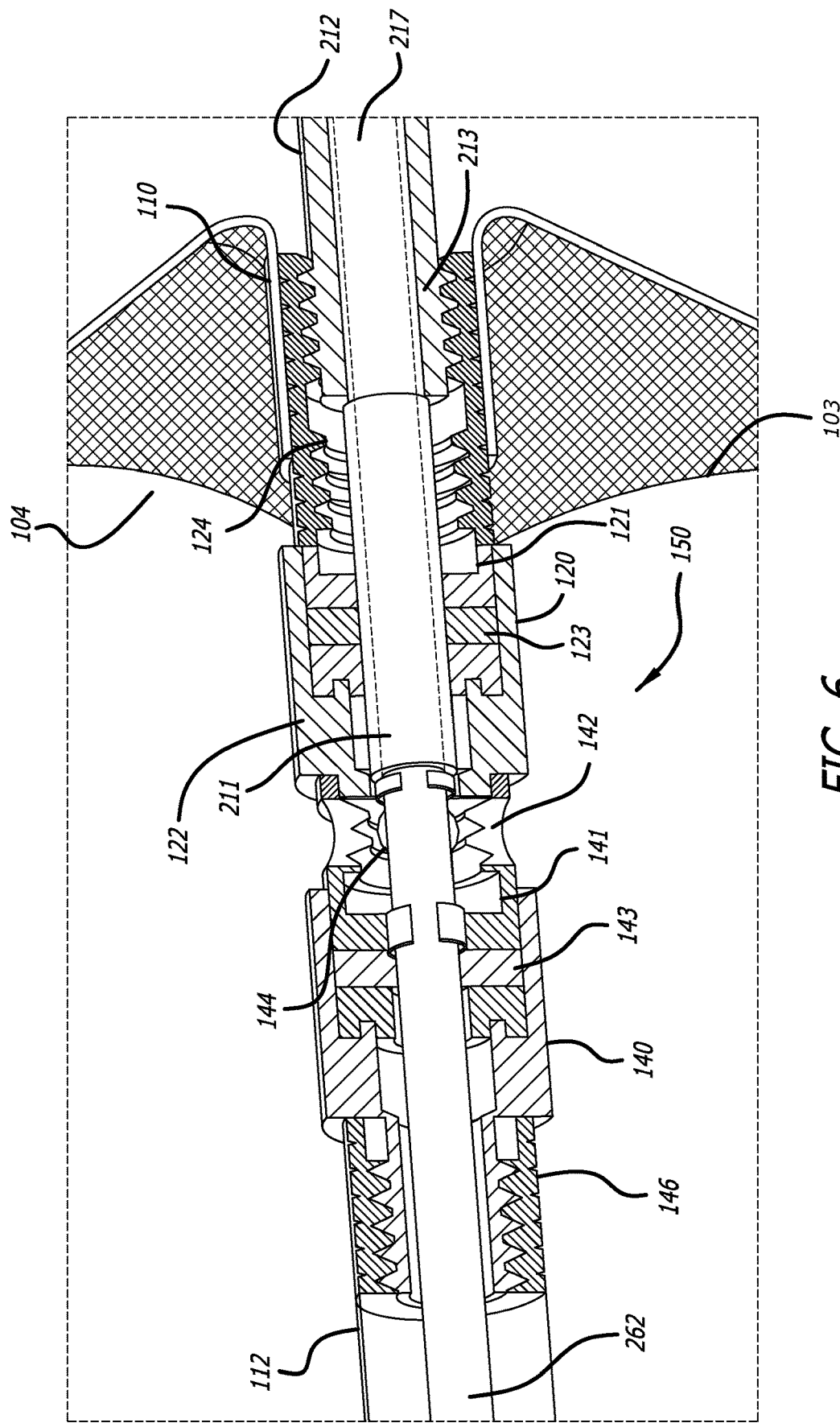
FIG. 6 illustrates a one-way valve assembly comprising a proximal valve and a distal valve, a catheter body of the outer catheter assembly, and a catheter body of the inner catheter assembly positioned inside the balloon assembly of FIG. 1.
Figure 13:
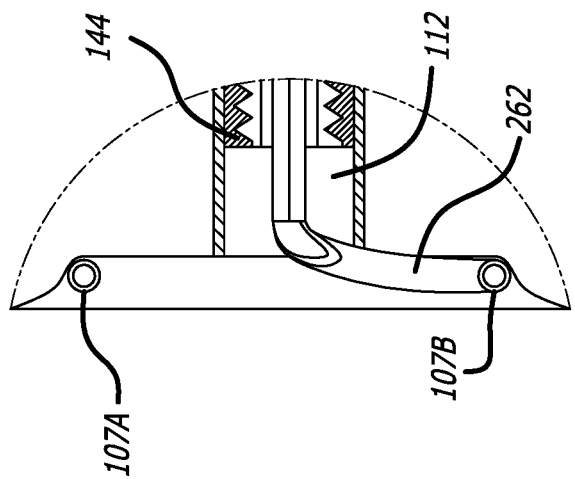
FIG. 13 illustrates the catheter body of the inner catheter assembly inside a distal port at the distal portion of the balloon assembly of FIG. 5.
Figure 12:
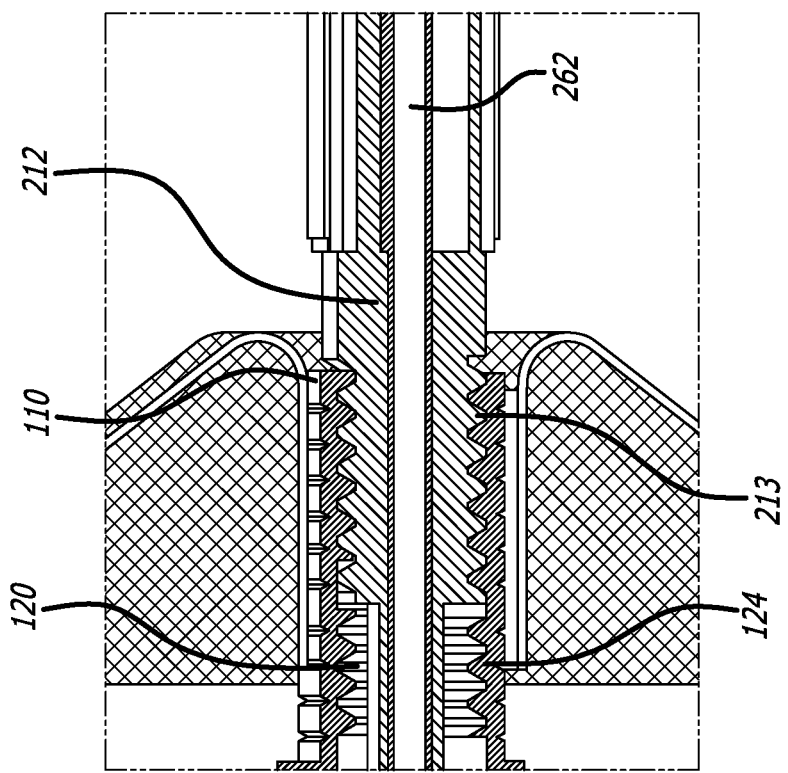
FIG. 12 illustrates threaded attachment between the catheter body of the outer catheter assembly with a proximal portion of the proximal valve at a proximal port of the balloon assembly.

In one example, as best seen in FIGS. 6 and 13, the distal portion 108 of the balloon assembly 100 comprises a distal port 112. The distal port 112 allows the entry of the catheter body 262 of the inner catheter assembly 260 inside the distal portion 108 of the balloon assembly 100 to deliver the adhesive or glue to fill the distal portion 108. Once catheter body 262 of the inner catheter assembly 260 enters inside the distal portion 108 of the balloon assembly 100 (e.g., during the initial manufacturing/configuration process), as can be seen in FIGS. 15-18 the catheter body 262 of the inner catheter assembly 260 may be spirally positioned from the bottom to the top of the distal portion 108 of the balloon assembly 100. As discussed previously, the distal portion 108 of the balloon assembly 100 comprises the membrane 106 (e.g., knit Dacron) on the top surface, as best seen in FIGS. 5 and 19B. Once catheter body 262 of the inner catheter assembly 260 delivers the adhesive or glue in the distal portion 108 of the balloon assembly 100, the adhesive or glue is contained under this knit membrane 106.

The balloon assembly 100 also may include a valve assembly 150 that allows inflation fluid and adhesive to be delivered to separate portions of the balloon assembly 100. Also, the valve assembly 150 allows the inner catheter assembly 260 and outer catheter assembly 210 can be disconnected from the balloon assembly 100 without causing deflation of the balloon assembly 100.

Specifically, the valve assembly 150 is configured to allow inflation fluid to pass into the proximal portion 104 from the outer catheter 210, but not into the distal portion 108 where it could dilute or cause premature hardening of the adhesive. The valve assembly 150 may be further configured to prevent inflation fluid from otherwise escaping from the proximal portion 104 so as to maintain the inflated state of the balloon assembly 100 after delivery. Finally, the valve assembly 150 can be further configured to provide each of these functions both when a distal portion of the catheter body 262 of the inner catheter assembly 260 is positioned through the valve assembly 150 and into the distal portion 108, and when the inner catheter assembly 260 is removed from the valve assembly 150 and balloon assembly 100, as described later in this specification.

Figure 11B:
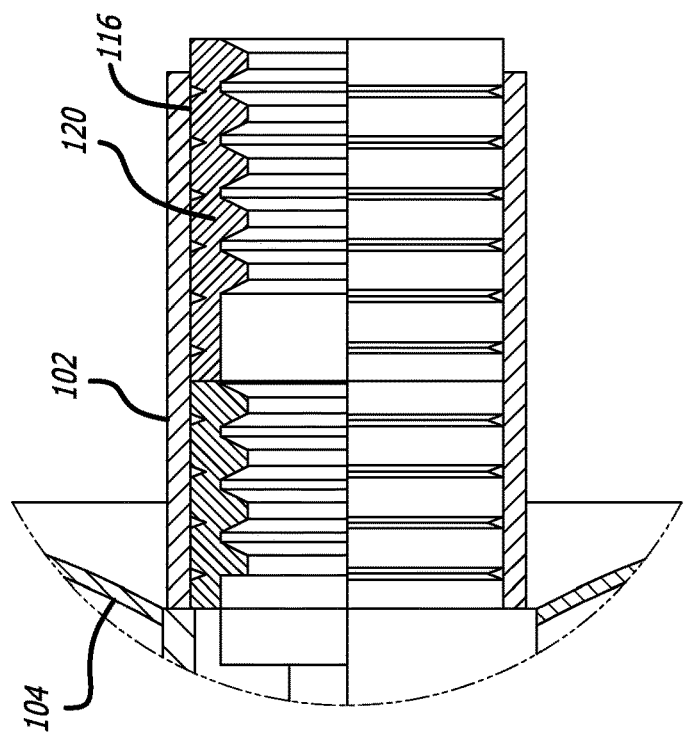
FIG. 11B illustrates the fabric of the balloon assembly relative to the valve assembly.
Figure 11A:
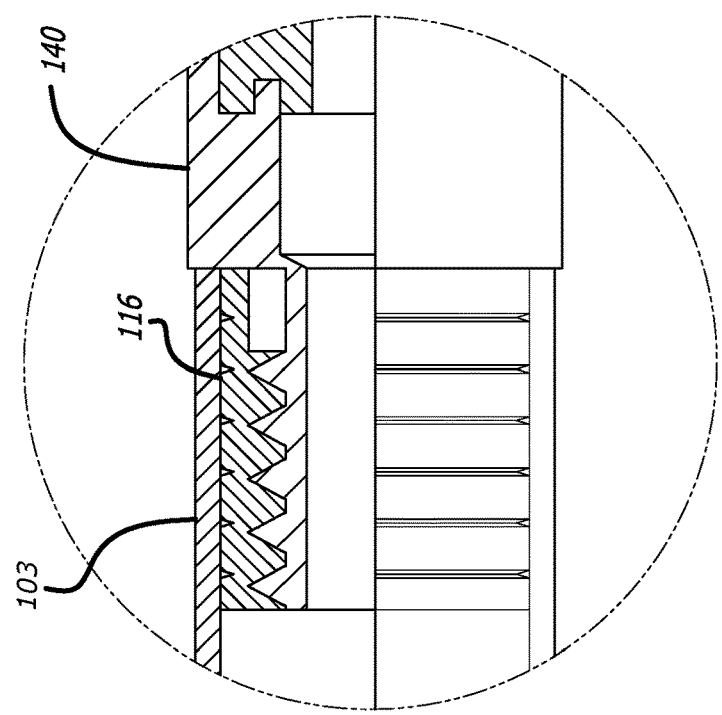
FIG. 11A illustrates adhesion between the membrane of the balloon assembly with the distal valve.

In one example, the endothelial growth material or fabric 102 disposed on the balloon membrane 103 of the balloon assembly 100 is attached to the top surfaces of a proximal valve 120 and distal valve 140 of the valve assembly 150 with UV-cured adhesive 116 to attach the balloon assembly 100 with the valve assembly 150. In one example, as best seen in FIG. 11A, the endothelial growth material or fabric 102 of the balloon assembly 100 is attached to the top surface of the distal valve 140 with UV cured glue 116. In one example, as best seen in FIG. 11B, the endothelial growth material or balloon fabric 102 of the balloon assembly 100 is attached to the top surface of the proximal valve 120 with UV cured glue 116.

In one example, as can be seen best in FIGS. 5 and 6, the valve assembly 150 includes a proximal valve 120 and a distal valve 140 which are connected to form a passage through the proximal portion 104 and into the distal portion 108 of the balloon assembly 100. The proximal valve 120 acts as a one-way valve, sealing around the outer catheter body 212 so that inflation fluid advanced from a distal end 211 of the outer catheter body 212 passes distally through the valve 120, through the apertures 144 positioned in the middle of the valve assembly 150, and into the proximal portion 104 to cause inflation. When the outer catheter body 212 is removed or detached later in the procedure, the proximal valve 120 prevents backflow of the inflation fluid towards the outer catheter assembly 210.

Similarly, the distal valve 140 acts as a valve, sealing around the catheter body 262 of the inner catheter assembly 260 so that adhesive advanced from the catheter body 262 of the inner catheter assembly 260 passes into the distal portion 108 without mixing with inflation fluid. This functionality may be particularly important to the adhesive absorbing membrane 106. If the adhesive absorbing membrane 106 becomes pre-saturated with inflation fluid, it may prevent the adhesive from being properly absorbed into the adhesive absorbing membrane 106 and therefore prevent the adhesive from being exposed on an outer surface of the membrane 106. When the catheter body 262 is removed from the balloon assembly 100 later in the procedure, the distal valve 140 closes and prevents the inflation fluid from escaping from the balloon assembly 100 into the patient.

Both valves 120 and 140 can be arranged in a linear passage or lumen to allow both the catheter body 212 and inner catheter assembly 260 to easily and coaxially pass through.

Structural details of the proximal valve 120 and distal valve 140 of the valve assembly 150 can be seen best in FIGS. 7A-10. In one example, the distal valve 140 (seen best in FIGS. 7A-7D) comprises a valve member 141 which allows the catheter body 262 of the inner catheter assembly 260 to pass through it and enter in the distal portion 108 of the balloon assembly 100 without allowing inflation fluid to further pass into the distal portion 108. In one example, the valve member 141 is composed of a flexible material (e.g., silicone or rubber) and has one or more slits extending axially through its thickness to as to create two or more valve flaps that can be pushed distally open by the catheter body 262 and close when the catheter body 262 is removed. As seen in the end view of FIG. 7B, two slits may be included in a cross or "+" shape to form four valve flaps, however, other numbers of slits are possible, such as 1, 3, 4, or 5.

Figure 7C:
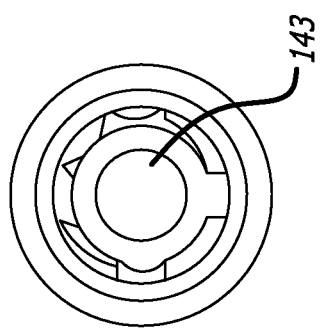
FIG. 7C illustrates a cross-sectional view of a gasket of FIG. 7A.
Figure 7A:
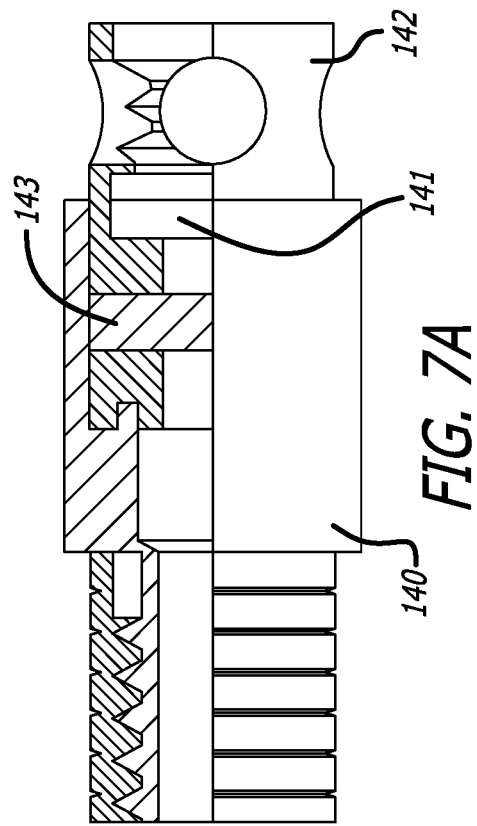
FIG. 7A illustrates the distal valve and its components.
Figure 7B:
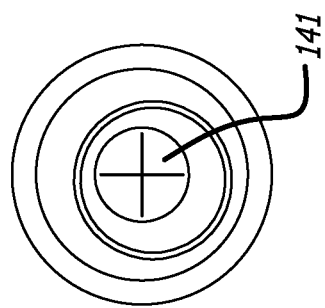
FIG. 7B illustrates a cross-sectional view of a valve member of FIG. 7A.
Figure 7D:
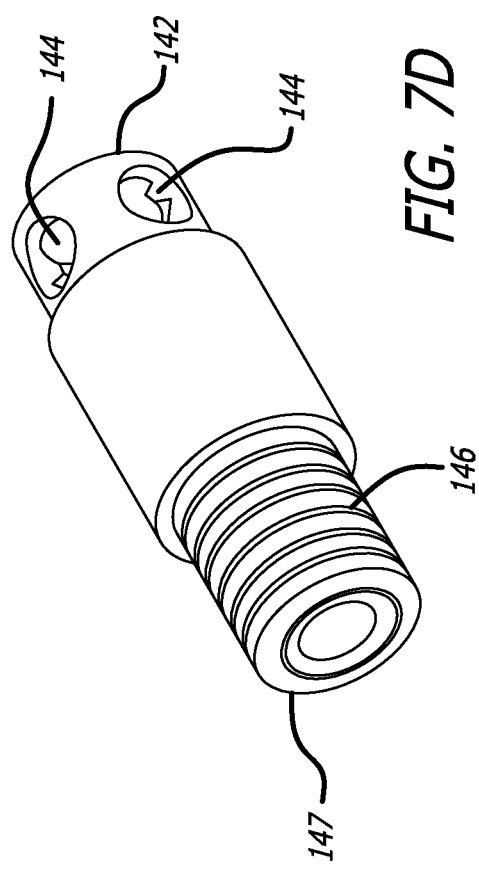
FIG. 7D illustrates a perspective view of the distal valve of FIG. 7A.

The distal valve 140 may further comprises a gasket 143 which has an opening therethrough and is sized to surround and engage the outside of the catheter body 262 of the inner catheter assembly 260. In one example, FIG. 7C shows a cross-sectional end view of the gasket 143 of the distal valve 140. The gasket 143 may provide both physical support to the catheter body 262 of the inner catheter assembly 260 and may provide an additional or secondary seal to the valve member 141 to prevent passage of inflation fluid into the distal portion 108. The gasket 143 may be composed of a flexible material (e.g., silicone or rubber) that allows it to compress or stretch as the catheter body 262 is pushed through it. Optionally, the passage through the gasket 143 may also be such that it closes or decreases in diameter nearly completely when the catheter body 262 is removed so that it further closes up after removal of the catheter body 262 of the inner catheter assembly 260.

The proximal valve 120, seen best in FIGS. 8A-8D, comprises a valve member 121 which is similar to the previously described valve member 141 and allows the outer catheter body 212 to pass through it so that the distal end 211 of the outer catheter body 212 is open to the interior of inflatable proximal portion 104. In one example, the valve member 121 is composed of a flexible material (e.g., silicone or rubber) and has one or more slits extending axially through its thickness to as to create two or more valve flaps that can be pushed open by the outer catheter body 212 and close when the outer catheter body 212 is removed. As seen in the end view of FIG. 8B, two slits may be included in a cross or "+" shape to form four valve flaps, however, other numbers of slits are possible, such as 1, 3, 4, or 5.

Figure 8C:
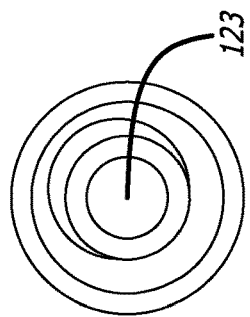
FIG. 8C illustrates a cross-sectional view of a gasket of FIG. 8A.
Figure 8A:
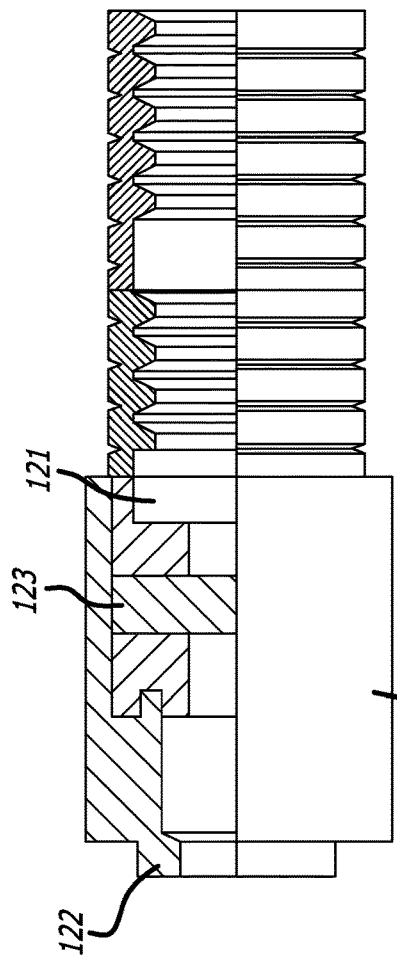
FIG. 8A illustrates the proximal valve and its components.
Figure 8B:
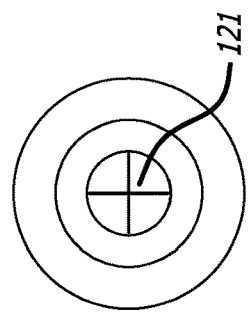
FIG. 8B illustrates a cross-sectional view of a valve member of FIG. 8A.
Figure 8D:
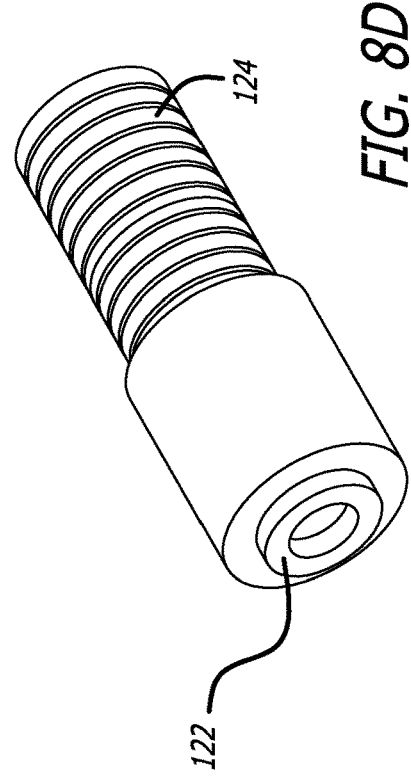
FIG. 8D illustrates a perspective view of the proximal valve of FIG. 8A.

The proximal valve 120 further comprises a gasket 123 similar to gasket 143, which has an opening therethrough and is sized to surround and engage the outside of the outer catheter body 212. In one example, FIG. 8C shows a cross-sectional end view of the gasket 123 of the distal valve 140. The gasket 123 may provide both physical support to the outer catheter body 212 and may provide an additional or secondary seal to the valve member 121 to prevent passage of inflation fluid proximally out of the proximal portion 104. The gasket 123 may be composed of a flexible material (e.g., silicone or rubber) that allows it to compress or stretch as the outer catheter body 212 is pushed through it. Optionally, the passage through the gasket 123 may also be such that it closes or decreases in diameter nearly completely when the outer catheter body 212 is removed so that it further closes up after removal of the outer catheter body 212.

The proximal valve 120 and the distal valve 140 are connected to each other via a tubular portion 142 that allows passage of the catheter body 262 of the inner catheter assembly 260 but also the inflation fluid from the outer catheter body 212 into the proximal portion 104. For example, the tubular portion 142 may have a generally tubular shape but may further include one or more apertures 144 through the wall of the tubular portion (e.g., 1, 2, 3, 4, 5, 6, or more apertures). Since the apertures 144 are positioned within the interior of the proximal portion 104, inflation fluid passing out of the distal end 211 of the outer catheter body 212 passes through the apertures 144 and into the proximal portion 104, causing it to inflate.

The proximal valve 120, the distal valve 140, and the tubular portion 142 of the valve assembly 150 can all be formed from a single unitary structural component. Alternately, the valve assembly 150 can be composed of several discrete components that are connected to each other. For example, the proximal valve 120, the distal valve 140, and the tubular portion 142 of the valve assembly 150 can all be connected via mating threads as seen in the figures, or via welding, laser welding, adhesives, or similar connection techniques.

Figure 20:
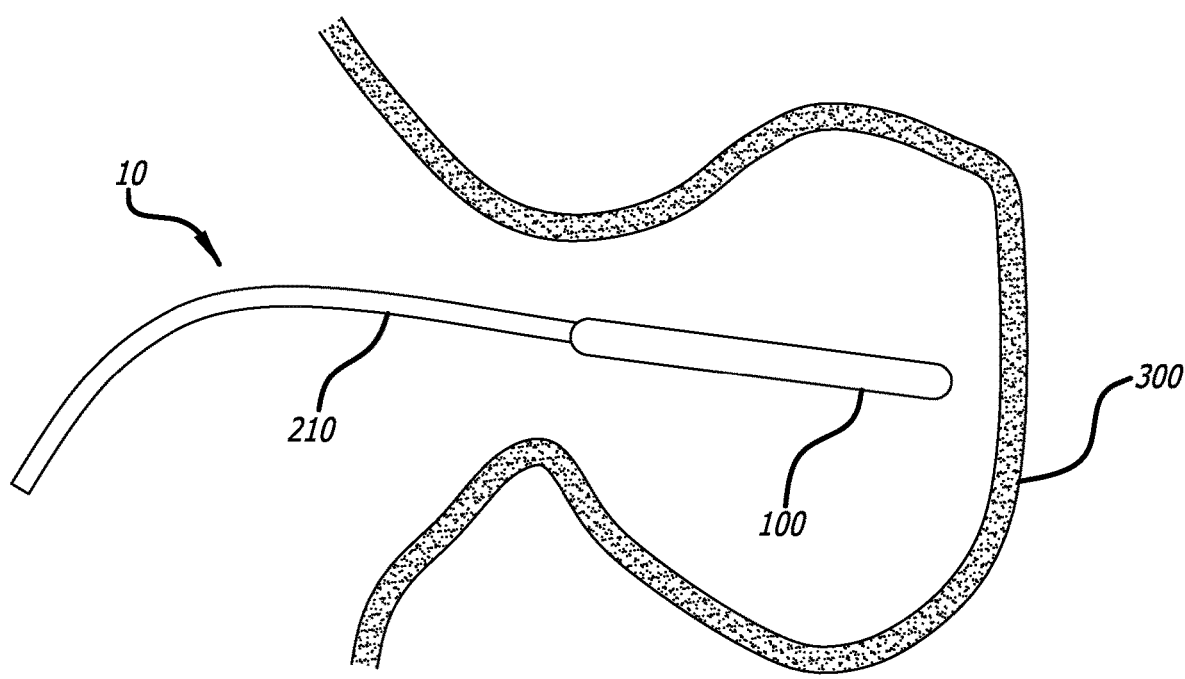
FIG. 20 illustrates the occlusive adhesive delivery system of FIG. 1 used in a treatment region.

The outer catheter assembly 210 is configured to position the balloon assembly 100 in its deflated state within a treatment site, for example, left atrial appendage, as shown in FIG. 20, inflate the balloon assembly 100, and then detach from the balloon assembly 100. The proximal portion 104 of the balloon assembly 100 is inflated with inflation fluid that travels within the lumen 217 of the outer catheter body 212. The outer catheter body 212 is also used as a conduit for the catheter body 262 of the inner catheter assembly 260 to deliver adhesive at the distal portion 108 of the balloon assembly 100, as can be seen in FIG. 4. In this respect, the outer catheter body has a generally elongated tubular structure with at least one passage extending therethrough. In one example, as seen best in FIG. 6, the diameter of the lumen 217 of the outer catheter body 212 is sized to allow the catheter body 262 of the inner catheter assembly 260 to be positioned inside it while also providing space surrounding the catheter body 262 of the inner catheter assembly 260 for passage of the inflation fluid. Hence, the catheter body 262 of the inner catheter assembly 260 can be coaxially positioned (or nearly so) within the lumen 217, allowing the lumen 217 to be used for two different purposes (i.e., inflation and positioning of the inner catheter assembly 260).

As best can be seen in FIGS. 2 and 4, the outer catheter assembly 210 may comprises a proximal connector assembly 214 (e.g., a Y adapter) that is connected to and in communication with the lumen 217 of the outer catheter body 212 to deliver inflation fluid into the lumen 217 of the outer catheter body 212 and further into the proximal portion 104 of the balloon assembly 100. In one example, as shown in FIG. 2, the connector assembly 214 is connected to a hub 216 of the outer catheter body 212 at one end (e.g., via threaded connection).

In one example, proximal connector assembly 214 includes two ports for allowing entry of the inner catheter assembly 260 and a syringe of inflation fluid. Port 218 can be used as a point of entry of the catheter body 262 of the inner catheter assembly 260, as shown in FIG. 4 and may have an appropriate connection mechanism at its end, such as a Tuohy Borst connector. Port 220, as shown in FIGS. 2 and 4, may be connected to a syringe (not shown in the figures) to deliver inflation fluid inside the outer catheter lumen 217 and to the proximal portion 104 of the balloon assembly 100 to inflate the balloon assembly 100. Hence, both ports 218 and 220 connect to the interior lumen 217 of the outer catheter assembly 210 via an internal "Y" passage. Port 218, as will be described later, can be used to facilitate delivery of adhesive.

The outer catheter assembly 210 further includes a detachment mechanism that allows the balloon assembly 100 to remain connected to and then be detached from the distal end of the outer catheter body 212. A variety of different detachment mechanisms can be used, such as a threaded detachment mechanism, a breakable tether mechanism, a latching mechanism with a pull wire, a tube that either melts with a heater coil or electrolytically dissolves when current is applied, or other detachment mechanisms known for use with delivery catheters.

An example of the threaded detachment mechanism is shown in FIGS. 2, 5, and 6, in which the outer catheter assembly 210 is threadably connected to the balloon assembly 100, and more specifically to a proximal section 124 of the valve assembly 150. As best seen in FIG. 6, a distal region of the outer catheter body 212 comprises a threaded portion 213 while an inner surface of the proximal section 124 of the valve assembly 150 includes mating threads. Hence, the outer catheter body 212 and its threaded portion 213 can screw into the mating threads of the proximal section 124 (e.g., by rotating the outer catheter assembly 210) of the valve assembly 150.

The outer catheter body 212 may include a distal end or region 211 that has a relatively smaller diameter than the threaded portion 213 and that extends distally beyond the distally threaded portion 213. When the threaded portion 213 is engaged with the proximal section 124 of the valve assembly 150, the distal end 211 extends into the proximal valve 120, through the valve member 121, and further through the gasket 123 so that the lumen 217 of the outer catheter body 212 is in communication with tubular portion 122, its apertures 144, and the interior of the proximal portion 104 of the balloon assembly 100.

Alternatively, the detachment system may comprise a collet along a proximal section of the distal port 112 of the balloon assembly 100 where the collet can be loosened to allow the catheter body 262 of the inner catheter assembly 260 to be removed from the distal port 112 of the balloon assembly 100 through the proximal port 110. Alternatively still, a mechanical engagement is used whereby the user can exert a certain amount of force to proximally pull the catheter body 262 of the inner catheter assembly 260 from the distal port 112 and remove it. Once the inner catheter body 262 of the inner catheter assembly 260 is removed from the distal port 112, the outer catheter body 212 is also removed from the proximal port 110 to leave the balloon 100 in place.

The inner catheter assembly 260, shown best in FIGS. 4, 6, and 15-18, is configured to deliver adhesive into the distal portion 108 of the balloon assembly 100. In one example shown in FIG. 4, the inner catheter assembly 260 comprises an elongated catheter body 262 containing a lumen and a catheter hub 261 located at a proximal end of the catheter body 262. The catheter hub 261 further comprises a port 263 that is in communication with the lumen within the catheter body 262, which allows a syringe (not shown) to be connected to inject adhesive within the lumen of the catheter body 262. The inner catheter assembly 260 passes through port 218, as shown in FIG. 4.

The catheter body 262 of the inner catheter assembly 260 is positioned inside the lumen 117 of the outer catheter assembly 210 through port 218 of the connector assembly 214 and spans past the distal end 211 of the outer catheter body 212 inside the balloon assembly 100, as best shown in FIGS. 4 and 6. The diameter of the catheter body 262 of the inner catheter assembly 260 is small enough to be positioned within the lumen 217 of the outer catheter body 212. The distal portion of the catheter body 262 of the inner catheter assembly 260 further spans through the valve assembly 150 and terminates within the distal portion 108 of the balloon assembly 100 and through port 112 of the distal portion 108, as shown in FIGS. 6 and 15-18.

In one example, the distal end of the catheter body 262 of the inner catheter assembly 260, as best seen in FIGS. 15-18, is positioned spirally around the interior of the distal portion 108 of the balloon assembly 100. Since the inner catheter assembly 260, outer catheter assembly 210, and the balloon assembly 100 are all initially advanced through a patient's vessels together, they will all be subjected to the curves of the patient's vasculature and therefore may cause the inner catheter assembly to move somewhat relative to the outer catheter assembly 210. The curved, excess length of the catheter body 262 of the inner catheter assembly 260 within the distal portion 108 may help maintain the distal end of the catheter body 262 within the distal portion 108, preventing it from otherwise pulling out of the valve assembly 150 prematurely. Optionally, the distal end portion of the catheter body 262 of the inner catheter assembly 260 may include a plurality of apertures along its length within the distal portion 108, allowing the adhesive to be more evenly distributed throughout the distal portion 108.

The lumen of the catheter body 262 may be composed of a material that prevents or does not begin polymerization of the adhesive. In one example, the lumen of the catheter body 262 is composed of PTFE (Teflon).

Preferably, the inner catheter assembly 260, the outer catheter assembly 210, and the balloon assembly 100 are all manufactured or delivered in a kit attached to each other as described above. However, alternate embodiments may allow these components to be assembled together by the physician prior to a procedure.

As previously discussed, the catheter body 262 of the inner catheter assembly 260 is configured to function as a conduit for delivering adhesive or glue to the distal portion 108 of the balloon assembly 100. Once the catheter body 262 of the inner catheter assembly 260 delivers the adhesive or glue in the distal portion 108 of the balloon assembly 100, the adhesive is contained under and within the membrane 106 positioned on the top surface of the distal portion 108 of the balloon assembly 100, as shown in FIGS. 5 and 15-18. The inner catheter assembly 260, and particularly the distal end of the catheter body 262 may include a coating that resists adhesion to the adhesive, helping to prevent it from becoming stuck in the distal portion 108.

Though the terms outer catheter 210 and inner catheter 260 are used to refer to the conduits to respectively deliver inflation fluid and adhesive, the outer catheter 260 and inner catheter 210 can also be referred to as and function as, respectively, an inflation fluid delivery member and an adhesive delivery member, an inflation fluid conduit and an adhesive conduit. Each of the outer catheter 210 and inner catheter 260 have a lumen or passage which respectively can function as an inflation fluid lumen/passage and an adhesive lumen/passage.

The outer catheter 210 and inner catheter 260 can also be referred to as a first catheter and a second catheter, respectively.

It should be appreciated that the outer catheter 210 and the inner catheter 260, in an alternate embodiment, could be constructed and used as a single catheter.

The delivery catheter assembly 200 may include a loader assembly 240, as shown in FIGS. 1, 3, and 4. The loader assembly 240 is an optional component that can act as a handle and can assist in loading the outer catheter assembly 210 into an introducer sheath (not shown) that has been previously placed into the patient. The loader assembly 240 and the outer catheter assembly 210 are allowed to slide relative to each other, and a threaded screw element 241 of the loader assembly 240 is screwed onto a proximal threaded connector thread of an introducer (not shown) that has been placed in a patient to connect the loader assembly 240 into the introducer. If the loader assembly 240 is positioned over the deflated balloon assembly 100 during attachment to the introducer (e.g. via threaded connector 241) it may also help prevent the balloon assembly 100 from being damaged as it is advanced into the introducer.

In one example, as shown in FIG. 3, the loader assembly 240 comprises a second connector assembly 242 which is connected at one end to a threaded connection mechanism 244 and at the other end to a port 248 (e.g., a Tuohy Borst connector). In one example, the threaded connection mechanism 244 is further connected to a tube 246, which may provide space for the deflated balloon assembly 100 as the loader assembly 240 is attached to the introducer. In one example, the tube comprises a threaded screw element 241 positioned at the distal end of the tube 246 that is screwed onto a proximal threaded connector thread of an introducer (not shown) which has been placed in a patient. In one example, as shown in FIGS. 3 and 4, the port 248 of the second connector assembly 242 is configured as a point of entry of the outer catheter assembly 210. The second connector assembly 242 further includes a port 250, as shown in FIG. 3 and can be used for introduction of saline or similar fluid into the introducer as needed.

At the end of the procedure, first, the catheter body 262 of the inner catheter assembly 260 may be pulled into the distal port 112 of the distal section 146 and then completely out of the balloon assembly 100. Then the outer catheter body 212 is detached (e.g., unscrewed) from the threaded proximal section 124 of the proximal valve 120 inside the proximal port 110 of the balloon assembly 100. In this way, both the catheter body 262 of the inner catheter assembly 260 and outer catheter body 212 are either pulled away or unscrewed at the end of the procedure once the proximal portion 104 is inflated with the inflation fluid and the adhesive is delivered inside the distal portion 108 of the balloon assembly 100. In this example, the inner catheter assembly 260 can be only partially withdrawn into the outer catheter assembly 100 so that the distal tip of the inner catheter assembly 260 is no exposed, or the inner catheter assembly 260 can be completely withdrawn from the outer catheter assembly 210 prior to its detachment. Alternately, the outer catheter body 212 can be detached (e.g., unscrewed) and the inner catheter assembly 260 can be removed from the balloon assembly 100 while the outer catheter assembly 210 is pulled proximally away from the balloon assembly 100.

It should be noted that hydrogel can also be used with previously described devices. For example, hydrogel may be included on the outer surface of the endothelial growth material or fabric 102, the balloon membrane 103, or the distal adhesive-absorbing membrane 106.

Different adhesives, such as tissue adhesives can be used with the devices and methods discussed in this specification. For example, cyanoacrylate-based adhesives such as 2-octyl-cyanoacrylate used in Dermabond or Surgiseal, or n-2-butyl-cyanoacrylate used in Histoacryl Blue and Periacryl, can be used. In another example, n-butyl-cyanoacrylate (nBCA) can be used. The tissue adhesive, such as nBCA, can be mixed with ethiodized oil (e.g., also known by the tradename Lipiodol and it is made up of poppyseed oil and iodine) to allow the combination to be visible under fluoroscopy. The ratio of these two components (e.g., a 9-to-1 ration of nBCA to ethiodized oil) can effect properties of the mixture including: the hardness, the visibility under fluoroscopy, and the amount of time the mix will cure. Ethiodized oil is water insoluble and does not polymerize the nBCA or other adhesive until the mixture is further mixed with blood.

In one example of the method of operation, the balloon assembly 100 is first prepared for use. The lumen of the inner catheter assembly 260 may be first flushed with saline to remove any residual air. The balloon assembly 100 may also be flushed with standard techniques used for balloon catheters. For example, a syringe filled with saline/contrast mixture (e.g., 70/30 ratio) attached to connector y port 220 and is slowly injected into the lumen 217 of the outer catheter 212, partially inflating the balloon assembly 100. Saline mixture is then drawn out pulling the air with it. The balloon assembly 100, outer catheter 212, and syringe are oriented such that the air migrates to the top of the syringe, purging the catheter lumen and balloon of air. An attached inline 3-way stopcock is closed, preventing re-introduction of any air.

Next, an introducer or outer delivery catheter may be advanced over a guidewire so that its distal end is in proximity to the left atrial appendage. Next, the guidewire is removed and the loader assembly 240 (if present) is connected to a proximal end of the introducer/catheter. The delivery catheter assembly 200, comprising the outer catheter assembly 210 and the inner catheter assembly 260, is proximally advanced through the loader 240 and into the introducer/catheter until the balloon assembly 100 is positioned distally outside of the introducer/catheter and within a left atrial appendage 300, as seen in FIG. 20.

Next, the balloon assembly 100 is inflated with inflation fluid transported by the outer catheter assembly 210. The inflation fluid can be injected via syringe into port 220 of the outer catheter assembly 210 so that it passes through lumen 217 of the outer catheter body 212, through the valve assembly 150, and into the proximal portion 104 of the balloon assembly 100, thereby inflating the balloon, as seen in FIG. 21. Preferably, the balloon assembly 100 is inflated and positioned such that it blocks or occludes the opening of the left atrial appendage 300. Hence, while the balloon assembly 100 may not fill every open portion of the appendage 300, blood is substantially prevented from entering the left atrial appendage.

The embodiments and methods of the present specification can be combined with or used in connection with the content found in U.S. Pub. Nos. 2018/0338767 and 2020/0138448, the contents of which are incorporated by reference in their entirety, disclose such an inflatable balloon assembly which comprises a retention structure at a proximal portion of the balloon to block the neck of the left atrial appendage and the delivery of adhesive to adhere the balloon to tissue.

Adhesive is delivered to the distal portion 108 of the balloon assembly 100 through the inner catheter assembly 260. A syringe containing adhesive can be connected to port 263 on the inner catheter assembly 260, causing the adhesive to pass through the lumen of the catheter body 262 and into the distal portion 108 of the balloon assembly 100. In some circumstances, it may be desirable to fully inflate the balloon assembly 100 prior to delivering the adhesive to the distal portion 108. In other circumstances, it may be desirable to only partially inflate the balloon assembly 100, inject the adhesive, and then further inflate the balloon assembly.

The exterior surface of the distal portion 108 of the balloon assembly 100 becomes saturated or damp with the adhesive as it moves through the membrane 106 from inside of the distal portion 108 to its outside. As the wetted membrane 106 contacts tissue within the left atrial appendage, the adhesive causes at least the distal balloon assembly 100 to adhere to left atrial appendage tissue. Depending on the amount of adhesive used, some adhesive may travel to exterior portions of the outside of the balloon assembly 100, causing areas beyond the distal membrane 106 to adhere as well.

Once the balloon assembly 100 has been inflated to a desired amount and adhered to the left atrial appendage, the inner catheter assembly 260 may be proximally and fully withdrawn from the outer catheter assembly 210. As seen in FIG. 22, the balloon assembly 100 is detached, for example, by unscrewing the outer catheter assembly 210 relative to the balloon assembly 100 (or via an alternate procedure if a different detachment mechanism is used). Depending on a variety of factors, such as the detachment mechanism, it may be possible to leave the inner catheter assembly 260 at least partially within the outer catheter assembly 210 and remove both components simultaneously after detachment. However, it may be desirable in such a circumstance to at least withdraw the distal tip of the catheter body 262 of the inner catheter assembly 260 so that any excess adhesive is not exposed to the patient's blood during the removal process. At the final stage of the procedure, the introducer is withdrawn from the treatment site.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An occlusion system for occluding a treatment site, comprising:
    an outer catheter having an elongated body and at least one lumen extending therethrough; an inner catheter disposed radially within the outer catheter;
    a balloon releasably connected to a distal end of the outer catheter via a detachment mechanism; and,
    an adhesive-absorbing membrane located at a distal portion of the balloon; the adhesive-absorbing membrane configured to absorb a predetermined volume of adhesive delivered through the inner catheter and to expose the adhesive along an outer surface of the adhesive-absorbing membrane.

2. The occlusion system of claim 1, wherein the adhesive-absorbing membrane is configured to absorb or contain about 0.1 to 1 ml of adhesive.

3. The occlusion system of claim 1, wherein the adhesive-absorbing membrane has a thickness within an inclusive range of about 0.001 inch to about 0.003 inch.

4. The occlusion system of claim 1, wherein the adhesive-absorbing membrane is composed of a 13 denier PET fiber woven to have about 120 courses per inch.

5. The occlusion system of claim 1, wherein pores of the adhesive-absorbing membrane have sizes in a range of about 3 microns-10 microns.

6. The occlusion system of claim 1, wherein the adhesive-absorbing membrane comprises a plurality of fibers forming a series of interlocking loops.

7. The occlusion system of claim 1, wherein a distal portion of the balloon comprises a depression, wherein the adhesive-absorbing membrane is positioned over the depression, and wherein the balloon is configured to limit external exposure of the adhesive to only the depression of the balloon.

8. The occlusion system of claim 1, wherein the inner catheter extends into the distal portion of the balloon.

9. The occlusion system of claim 8, further comprising a valve assembly positioned within the balloon so as to separate an interior of the balloon from the adhesive-absorbing membrane, the valve assembly comprising a first valve configured to seal around the outer catheter and a second valve configured to seal around the inner catheter.

10. The occlusion system of claim 9, wherein the at least one lumen of the outer catheter comprises an inflation lumen sized and configured to allow passage of inflation fluid into the interior of the balloon while the inner catheter is positioned within the inflation lumen.

11. An occlusion system for occluding a treatment site in a heart, comprising:
    an outer catheter having an elongated body and an inflation lumen extending therethrough; and,
    a balloon releasably connected to a distal end of the outer catheter via a detachment mechanism; the balloon comprising an inflatable portion configured to receive inflation fluid and a distal depression configured to accept adhesive;
    a first valve preventing release of the inflation fluid outside of the inflatable portion of the balloon, and a second valve preventing release of the inflation fluid into the distal depression.

12. The occlusion system of claim 11, wherein the first valve and the second valve are arranged in a linear passage.

13. The occlusion system of claim 12, wherein the first valve is configured to engage the outer catheter and wherein the second valve is configured to engage an inner catheter positioned within the inflation lumen of the outer catheter.

14. The occlusion system of claim 13, wherein the inner catheter is configured to deliver adhesive to the distal depression and wherein the outer catheter is configured to deliver inflation fluid through the inflation lumen while the inner catheter is positioned within the inflation lumen.

15. The occlusion system of claim 11, wherein the distal depression comprises an adhesive-absorbing membrane configured to absorb a volume of an adhesive and expose the adhesive on an outer surface of the adhesive-absorbing membrane.

16. The occlusion system of claim 15, wherein the adhesive-absorbing membrane is woven to have a thickness within an inclusive range of about 0.001 inch to about 0.003 inch and has a pore size within an inclusive range of about 3-10 microns.

17. A method for occluding blood flow in a left atrial appendage in a heart of a patient, comprising:
    advancing a balloon into a left atrial appendage, the balloon comprising a distal depression;
    inflating at least a portion of the balloon via an inflation lumen from an outer catheter;
    delivering adhesive to the distal depression of the balloon;
    absorbing the adhesive with an adhesive-absorbing membrane positioned over distal depression of the balloon so that the adhesive is exposed on an outer surface of the adhesive-absorbing membrane; and,
    detaching the outer catheter from the balloon.

18. The method of claim 17, further comprising preventing inflation fluid from the balloon from entering into the distal depression of the balloon.

19. The occlusion system of claim 7, wherein, in a delivery configuration, a distal portion of the inner catheter forms a spiral within the depression of the balloon.

20. The occlusion system of claim 11, wherein the first valve and the second valve are interconnected together in linear alignment.

* * * * *